United States Patent [19]

Götschi

[11] Patent Number: 5,036,064
[45] Date of Patent: Jul. 30, 1991

[54] CEPHALOSPORINS WITH SULFUR-CONTAINING OXYIMINO SIDE CHAIN

[75] Inventor: Erwin Götschi, Reinach, Switzerland

[73] Assignee: Hoffmann-La Roche Inc., Nutley, N.J.

[21] Appl. No.: 229,960

[22] Filed: Aug. 9, 1988

[30] Foreign Application Priority Data

Aug. 14, 1987 [CH] Switzerland ............... 3133/87
Dec. 3, 1987 [CH] Switzerland ............... 4726/87

[51] Int. Cl.$^5$ ............... C07D 501/36; A61K 31/545
[52] U.S. Cl. ............... 514/206; 540/227; 540/222; 540/230
[58] Field of Search ............... 540/222, 227; 514/202, 514/206, 203

[56] References Cited

U.S. PATENT DOCUMENTS 4,808,711 2/1989 Shimizu et al. ............... 540/222

FOREIGN PATENT DOCUMENTS 0150507 7/1985 European Pat. Off. .
0189287 7/1986 European Pat. Off. .

OTHER PUBLICATIONS

Chemical Abstracts, vol. III, 39101(u) (1989).

Primary Examiner—Nicholas S. Rizzo
Attorney, Agent, or Firm—George M. Gould; Bernard S. Leon; Ellen Ciambrone Coletti

[57] ABSTRACT

Antibacterial compounds of the formula

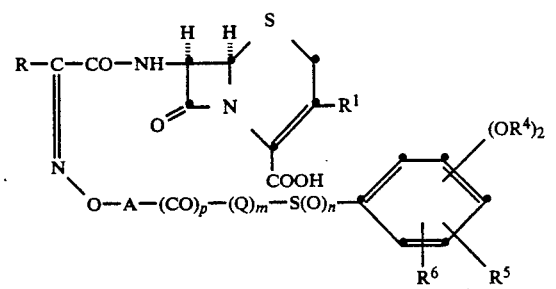

wherein R is a mononuclear carbocyclic aromatic group, a 5-membered aromatic heterocyclic group which contains as the hetero (non-carbon) ring member(s) an oxygen or sulphur atom or an imino or lower alkylimino group and, optionally, one or two nitrogen atoms, or a 6-membered aromatic heterocyclic group which contains one to three nitrogen atoms as the hetero ring member(s); $R^1$ is hydrogen or a 3-substituent which is usable in cephalosporin chemistry; A is lower alkylene or $C_{3-7}$-cycloalkylene which is optionally substituted with carboxy, carbamoyl, lower alkylcarbamoyl or di(lower alkyl)carbamoyl; Q is lower alkylene or $C_{3-7}$-cycloalkylene which is optionally substituted with carboxy, carbamoyl, lower alkylcarbamoyl or di(lower alkyl)carbamoyl, or the group $-NR^2-$ or $-NR^2NR^3-$; $R^2$ and $R^3$ are independently hydrogen or lower alkyl; p and m are the zero or 1, n is zero, 1 or 2; $R^4$ is hydrogen, lower alkanoyl or tri(lower alkyl)silyl; two $R^4$ groups together represent diphenylmethylene; $R^5$ is hydrogen, lower alkyl, hydroxy, lower alkoxy, halogen, nitro, $-OCOR^7$, $-OCOOR^{71}$, $-N(R^7)_2$, $-NHCOR^7$, $-NHCOOR^{71}$, $-COR^7$, $-SR^7$, $-SOR^7$, $-SO_2R^7$, $-SO_3H$, $-COOR^7$ or $-CON(R^7)_2$; $R^6$ is hydrogen, lower alkyl or halogen, $R^7$ is hydrogen or lower alkyl; $R^{71}$ is lower alkyl, and the two $-OR^4$ groups are attached to the phenyl ring via adjacent carbon atoms, as well as readily hydrolyzable esters and pharmaceutically acceptable salts of these compounds and hydrates of compounds of formula I and of their esters and salts.

49 Claims, No Drawings

CEPHALOSPORINS WITH SULFUR-CONTAINING OXYIMINO SIDE CHAIN

DESCRIPTION OF THE INVENTION

The present invention is concerned with acyl derivatives, and more specifically antibacterial agents of the formula

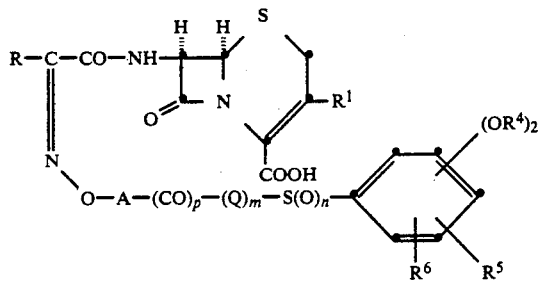

in which R is a mononuclear, carbocyclic aromatic group, a 5-membered, aromatic heterocyclic group which contains as the hetero (non-carbon) ring member(s) an oxygen or sulphur atom or an imino or lower alkylimino group and, optionally, one or two nitrogen atoms, or a 6-membered aromatic heterocyclic group which contains one to three nitrogen atoms as the hetero ring member(s); $R^1$ is hydrogen or a 3-substituent which is usable in cephalosporin chemistry; A is lower alkylene or $C_{3-7}$-cycloalkylene which is optionally substituted with carboxy, carbamoyl, lower alkylcarbamoyl or di(lower alkyl)carbamoyl; Q is lower alkylene or $C_{3-7}$-cycloalkylene which is optionally substituted with carboxy, carbamoyl, lower alkylcarbamoyl or di(lower alkyl)carbamoyl, or the group $-NR^2-$ or $-NR^2N-R^3-$; $R^2$ and $R^3$ are independently hydrogen or lower alkyl; p and m are zero or 1; n is zero, 1 or 2; $R^4$ is hydrogen, lower alkanoyl or tri(lower alkyl)silyl, or two of $R^4$ together represent diphenylmethylene: $R^5$ is hydrogen lower alkyl, hydroxy, lower alkoxy, halogen, nitro, $-OCOR^7$, $-OCOOR^{71}$, $-N(R^7)_2$, $-NHCOR^7$, $-NHCOOR^{71}$, $-COR^7$, $-SR^7$, $-SOR^7$, $-SO_2R^7$, $-SO_3H$, $-COOR^7$ or $-CON(R^7)_2$; $R^6$ is hydrogen, lower alkyl or halogen; $R^7$ is hydrogen or lower alkyl; and $R^{71}$ is lower alkyl, and the two groups $-OR^4$ groups are attached to the phenyl ring via adjacent carbon atoms, as well as with readily hydrolyzable esters and pharmaceutically acceptable salts of these compounds and hydrates of compounds of formula I and of their esters and salts.

The compounds of formula I are present preferably in the syn-isomeric form. However, they can also be present as mixtures with the corresponding anti-isomeric form in which the syn-isomeric form predominates.

In addition to the above compounds, this invention also encompasses pharmaceutical compositions containing such compounds as therapeutically active ingredients and the use of such compounds in the treatment of bacterial infections.

The term "lower" means having a maximum of 7 preferably a maximum of 4, carbon atoms. The term "alkyl" denotes straight-chain or branched saturated hydrocarbon residues such as methyl, ethyl, propyl, isopropyl and t-butyl. The term "alkylene" denotes corresponding hydrocarbon residues having two free valencies such as methylene, dimethylene, ethylidene, propylidene, butylidene, isopropylidene and 1,2-isobutylene. The term "alkoxy" denotes alkyl groups attached via an oxygen atom, such as methoxy and ethoxy. The term "alkanoyl" denotes residues derived from straight-chain or branched, saturated fatty acids such as formyl and acetyl. The term "$C_{3-7}$-cycloalkyl" denotes saturated, cyclic hydrocarbon residues, i.e., cycloalkyl residues which are optionally substituted with alkyl groups such as cyclopropyl, cyclobutyl, cyclohexyl and methylcyclopropyl. The term "$C_{3-7}$-cycloalkylene" denotes cyclic hydrocarbon residues having two free valencies, such as cyclopropylidene, cyclobutylidene, cyclohexylidene and 2-methylcyclopropylidene.

The term "halogen" denotes all four forms: chlorine, fluorine, bromine and iodine, with chlorine being preferred.

The term "mononuclear, carbocyclic aromatic group" refers to unsubstituted or substituted phenyl groups, preferably phenyl groups which are optionally mono-, di- or trisubstituted with halogen, hydroxy, nitro, amino, cyano, trifluoromethyl, lower alkyl or lower alkoxy.

The 5-membered, aromatic heterocyclic groups are preferably unsubstituted or substituted with halogen, hydroxy nitro, amino, cyano, trifluoromethyl, lower alkoxy or lower alkoxy. They are preferably substituted, with an amino group. Examples of such heterocycles, which can be unsubstituted or substituted, include the following: furyl, thienyl, oxazolyl, thiazolyl, thiadiazolyl, imidazolyl, pyrazolyl and triazolyl. Preferred heterocyclic groups are: 2-amino-4-thiazolyl, 5-amino-1,2,4-thiadiazolyl, 2-amino-4-oxazolyl and 2-amino-4-imidazolyl.

The 6-membered, aromatic heterocyclic groups are preferably unsubstituted or substituted with halogen, hydroxy, nitro, amino, cyano, trifluoromethyl, lower alkyl or lower alkoxy. Examples of such heterocycle, which can be substituted or unsubstituted, include: pyridyl, pyrimidinyl and triazinyl. The 2-amino-6-pyridyl group is an especially preferred 6-membered heterocyclic group.

The term "3-substituent which is usable in cephalosporin chemistry" denotes the usual substituents which are present in the 3-position of the cephalosporin skeleton of therapeutically active cephalosporins. This term preferably denotes lower alkyl such as methyl, lower alkoxy such as methoxy, halogen such as chlorine, or the group $-CH_2R'$ or $-CH_2S-R''$ in which R' means azido, lower alkanoyloxy, carbamoyloxy, N-(lower alkyl)carbamoyloxy, N,N-di-(lower alkyl)carbamoyloxy or a N-containing heterocyclic group attached via a nitrogen atom and R'' means a heterocyclic group attached via a carbon atom.

The term "N-containing heterocyclic group" preferably denotes saturated, partially unsaturated and aromatic heterocyclic groups containing up to 4 nitrogen atoms as the hetero atom(s). They are preferably 5- or 6-membered and can be fused by a 5- or 6-membered cycloalkane ring or by a benzene ring, and preferably unsubstituted or substituted with lower alkyl or carbamoyl. The nitrogen atom by which the N-containing heterocyclic group is attached can also be quaternary substituted. 5-Methyl-2-tetrazolyl and pyridinium-1-yl are examples of N-containing heterocyclic groups.

The term "heterocyclic group" preferably means monocyclic, especially 5- and 6-membered, partially unsaturated or aromatic heterocyclic groups which preferably contain as the hetero atom(s) an oxygen or sulphur atom and/or 1-4 nitrogen atoms, as well as bicyclic, especially 8-10 membered, partially unsaturated or aromatic heterocyclic groups which preferably contain as the hetero atom(s) an oxygen or sulphur atom and/or 1-5 nitrogen atoms. These groups, are preferably unsubstituted or mono-, di- or tri-substituted with lower alkyl, lower alkoxy, lower alkanediyl, halogen, trifluoromethyl, hydroxy, oxo, carboxy, lower alkoxycarbonyl, carbamoyl, N-(lower alkyl)carbamoyl, N,N-di(lower alkyl)carbamoyl, amino, lower alkylamino, di(lower alkyl)amino, mercapto, lower alkylthio, lower hydroxyalkyl, lower aminoalkyl, lower alkylamino-lower alkyl, di(lower alkyl)amino-lower alkyl, lower carboxyalkyl, carbamoyl-lower alkyl, N-(lower alkyl)-carbamoyl-lower alkyl, N,N-di(lower alkyl)-carbamoyl-lower alkyl or sulpho-lower alkyl.

The monocyclic heterocyclic groups are preferably aromatic and preferably substituted with lower alkyl, halogen, hydroxy, oxo, carboxy, carbamoyl, amino, lower alkylamino, di(lower alkyl)amino, mercapto, lower alkylthio, lower hydroxyalkyl, lower aminoalkyl, lower alkylamino-lower alkyl, di(lower alkyl)amino-lower alkyl, lower carboxyalkyl, carbamoyl-lower alkyl, N-(lower alkyl)-carbamoyl-lower alkyl, N,N-di(lower alkyl)-carbamoyl-lower alkyl or sulpho-lower alkyl. Tetrazolyl, triazolyl, thiadiazolyl and triazinyl are mentioned merely as examples. Preferred among such groups are: 1-methyl-tetrazol-5-yl, 1-(2-hydroxyethyl)-5-tetrazolyl, 5-methyl-1,3,4-thia-diazol-2-yl, 1,2,3-thiadiazol-5-yl, 1,4,5,6-tetrahydro-4-methyl-5,6-dioxo-as-triazin-3-yl, 2,5-dihydro-6-hydroxy-2-methyl-5-oxo-as-triazin-3-yl and 1,2,5,6-tetrahydro-2-methyl-5,6-dioxo-as-triazin-3-yl.

The bicyclic groups are preferably aromatic. They are preferably unsubstituted or substituted with amino, lower alkylamino, di(lower alkyl)amino, carboxy, lower alkoxycarbonyl, carbamoyl, N-(lower alkyl)carbamoyl, N,N-di-(lower alkyl)carbamoyl, lower alkyl, trifluoromethyl or 3,4-alkanediyl. They are also preferably 9-membered and have 2 to 4 nitrogen atoms as the hetero ring members.

In a preferred embodiment, A represents lower alkylidene and n is 2, and either m or p is zero or m and p are 1. Q is the group $-NR^2NR^3-$ and $R^2$ and $R^3$ are hydrogen. $R^4$, $R^5$ and $R^6$ are preferably hydrogen. Preferably, the two $-OR^4$ groups are situated in positions 3 and 4 of the phenyl ring.

In an especially preferred embodiment, A represents methylene or isopropylidene.

Preferred substituents in the 7-position of a cephalosporin of formula I are as follows:

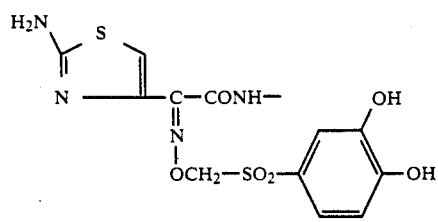

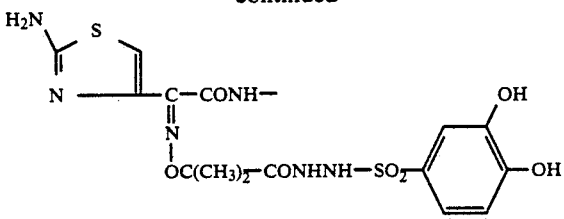

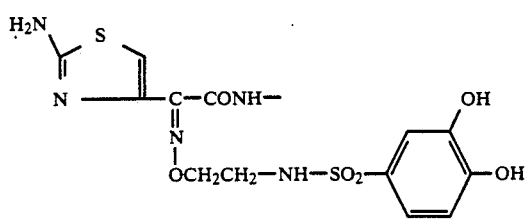

$R^1$ preferably is hydrogen, lower alkyl, lower alkoxy, halogen, or the groups $-CH_2R'$ or $-CH_2-S-R''$ in which $R'$ is azido, lower alkanoyloxy, carbamoyloxy, N-(lower alkyl)carbamoyloxy, N,N-di(lower alkyl)carbamoyloxy or a N-containing heterocyclic group is attached via a nitrogen atom, and $R''$ is a heterocyclic group attached via a carbon atom.

In an especially preferred embodiment, $R^1$ represents the group $-CH_2-S-R''$. $R''$ preferably is a bicyclic, 8- to 10-membered partially unsaturated or aromatic heterocyclic group which contains an oxygen or sulphur atom and/or 1-5 nitrogen atoms as the hetero ring member(s). The heterocyclic group $R''$ in this case is preferably unsubstituted or mono-, di- or trisubstituted with amino, lower alkyl, lower alkoxy, lower alkanediyl, halogen, trifluoromethyl, hydroxy, oxo, carboxy, lower alkoxycarbonyl, carbamoyl, N-(lower alkyl)carbamoyl or N,N-di(lower alkyl)carbamoyl.

In an especially preferred embodiment, the heterocyclic group $R''$ has the formula

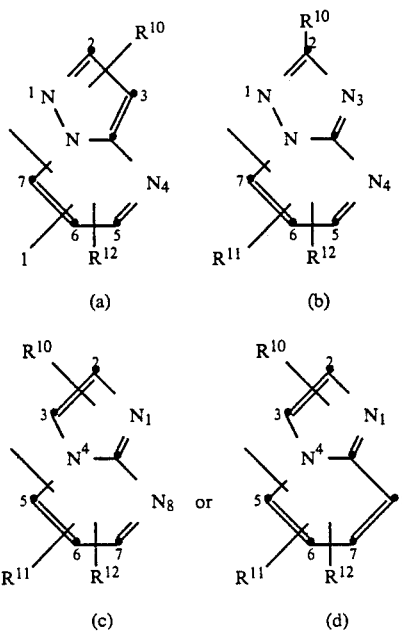

wherein $R^{10}$ is hydrogen, amino, carboxy, lower alkoxycarbonyl, carbamoyl, hydroxymethyl, N-(lower alkyl)carbamoyl or N,N-di(lower alkyl)carbamoyl and $R^{11}$ and $R^{12}$ each are hydrogen, lower alkyl or trifluoromethyl or together represent a 3,4-alkanediyl group.

The heterocyclic groups of formulae (a) and (b) are preferably linked via the 5- or the 7-position, especially via the 7-position. The heterocyclic group of formula (c) is preferably linked via the 5- or 7-position, especially via the 5-position, and that of formula (d) is preferably linked via the 5- or 8-position, especially via the 5-position. The substituent $R^{10}$ is preferably situated in the 3-position when the heterocyclic group corresponds to formula (a), (c) or (d); $R^{10}$ preferably is carbamoyl or hydroxymethyl; $R^{11}$ preferably is hydrogen; and $R^{12}$ is preferably lower alkyl or trifluoromethyl especially methyl.

In further especially preferred embodiments, R" is 2-carbamoyl-5-methyl-s-triazolo[1,5-a]pyrimidin-7-yl or 2-(hydroxymethyl)-5-methyl-s-triazolo[1,5-a]pyridin-7-yl.

R preferably is 2-amino-4-thiazolyl.

Examples of compounds within the scope of the present invention, which are especially preferred, are the following:

(6R,7R)-7-[(Z)-2-(2-amino-4-thiazolyl)-2-[[[(3,4-dihydroxyphenyl)sulphonyl]methoxy]imino]acetamido]-3-[[(2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid, and (6R,7R)-7-[(Z)-2-(2-amino-4-thiazolyl)-2-[[[(3,4-dihydroxyphenyl)sulphonyl]methoxy]imino]acetamido]-3-[[[2-(hydroxymethyl)-5-methyl-s-triazolo[1,5-a]pyrimidin-7-yl]thio]methyl]-8-oxo-5-thia-1-azabicyclo[4.2.0]oct-2-ene-2-carboxylic acid, as well as their pharmaceutically acceptable salts.

Additional compounds in accordance with the invention are the following and their pharmaceutically acceptable salts:

(6R,7R)-7-[(Z)-2-(2-amino-4-thiazolyl)-2-[[[(3,4-dihydroxyphenyl)sulphonyl]methoxy]imino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid, (6R,7R)-3-(acetoxymethyl)-7-[(Z)-2-(2-amino-4-thiazolyl)-2-[[[(3,4-dihydroxyphenyl)sulphonyl]methoxy]imino]acetamido]-8-oxo-5-thia-1-azabicyclo[4.2.0]oct-2-ene-2-carboxylic acid, (6R,7R)-7-[(Z)-2-(2-amino-4-thiazolyl)-2-[[[(3,4-dihydroxyphenyl)sulphonyl]methoxy]imino]acetamido]]-3-[[(2-carboxy-5-methyl-s-triazolo[1,5-a]pyrimidin-7-yl)thio]methyl]-8-oxo-5-thia-1-azabicyclo[4.2.0]oct-2-ene-2-carboxylic acid, (6R,7R)-7-[(Z)-2-(2-amino-4-thiazolyl)-2-[[[(3,4-dihydroxyphenyl)sulphonyl]methoxy]imino]acetamido]-3-(azidomethyl)-8-oxo-5-thia-1-azabicyclo[4.2.0]oct-2-ene-2-carboxylic acid, 1-[(6R,7R)-7-[(Z)-2-(2-amino-4-thiazolyl)-2-[[[(3,4-dihydroxyphenyl)sulphonyl]methoxy]imino]acetamido]-2-carboxy-8-oxo-5-thia-1-azabicyclo[4.2.0]oct-2-ene-3-yl]pyridinium betaine, (6R,7R)-7-[(Z)-2-(2-amino-4-thiazolyl)-2-[[[(3,4-dihydroxyphenyl)sulphonyl]methoxy]imino]acetamido]-3-[[(5-methyl-1,3,4-thiadiazol-2-yl)thio]methyl]-8-oxo-5-thia-1-azabicyclo[4.2.0]oct-2-ene-2-carboxylic acid, (6R,7R)-7-[(Z)-2-(2-amino-4-thiazolyl)-2-[[[(3,4-dihydroxyphenyl)sulphonyl]methoxy]imino]acetamido]-3-[[(3-carbamoyl-5-methylpyrazolo[1,5-a]pyrimidin-7-yl)thio]methyl]-8-oxo-5-thia-1-azabicyclo[4.2.0]oct-2-ene-2-carboxylic acid, (6R,7R)-7-[(Z)-2-(2-amino-4-thiazolyl)-2-[[[(3,4-dihydroxyphenyl)sulphonyl]methoxy]imino]acetamido]-3-[[(3-carbamoyl-7-(trifluoromethyl)pyrazolo[1,5-a]pyrimidin-5-yl)thio]methyl]-8-oxo-5-thia-1-azabicyclo[4.2.0]oct-2-ene-2-carboxylic acid, (6R,7R)-7-[(Z)-2-(2-amino-4-thiazolyl)-2-[[1-[3-[((3,4-dihydroxyphenyl)sulphonyl)carbazolyl]-1-methylethoxy]imino]acetamido]-3-[[(2-carbamoyl)-5-methyl-s-triazolo[1,5-a]pyrimidin-7-yl)thio]methyl]-8-oxo-5-thia-1-azabicyclo[4.2.0]oct-2-ene-2-carboxylic acid, (6R,7R)-7-[(Z)-2-(2-amino-4-thiazolyl)-2-[[[(3,4-dihydroxyphenyl)sulphonyl]methoxy]imino]acetamido]-3-[[(2-(methoxycarbonyl)-5-methyl-s-triazolo[1,5-a]pyrimidin-7-yl)thio]methyl]-8-oxo-5-thia-1-azabicyclo[4.2.0]oct-2-ene-2-carboxylic acid, (6R,7R)-7-[(Z)-2-(2-amino-4-thiazolyl)--2-[[[(3,4-dihydroxyphenyl)sulphonyl]methoxy]imino]acetamido]-3-[[(7-methylpyrazolo[1,5-a]pyrimidin-5-yl)thio]methyl-8-oxo-5-thia-1-azabicyclo[4.2.0]oct-2-ene-2-carboxylic acid, (6R,7R)-7-[(Z)-2-(2-amino-4-thiazolyl)-2-[[[(3,4-dihydroxyphenyl)sulphonyl]methoxy]imino]acetamido]-3-[[(5-methylpyrazolo[1,5-a]pyrimidin-7-yl)thio]methyl]-8-oxo-5-thia-1-azabicyclo[4.2.0]oct-2-ene-2-carboxylic acid, (6R,7R)-7-[(Z)-2-(2-amino-4-thiazolyl)-2-[[[(3,4-dihydroxyphenyl)sulphonyl]methoxy]imino]acetamido]-3-[[(3-carboxy-7-methylpyrazolo[1,5-a]pyrimidin-5-yl)thio]methyl]-8-oxo-5-thia-1-azabicyclo[4.2.0]oct-2-ene-2-carboxylic acid, (6R,7R)-7-[(Z)-2-(2-amino-4-thiazolyl)-2-[[[(3,4-dihydroxyphenyl)sulphonyl]methoxy]imino]acetamido]-3-[[(2,5-dimethylpyrazolo[1,5-a]pyrimidin-7-yl)thio]methyl]-8-oxo-5-thia-1-azabicyclo[4.2.0]oct-2-ene-2-carboxylic acid, (6R,7R)-7-[(Z)-2-(2-amino-4-thiazaolyl)-2-[[[(3,4-dihydroxyphenyl)sulphonyl]methoxy]imino]acetamido]-3-[[(2,8-bis(trifluoromethyl)-4-quinolinyl]thio]methyl-8-oxo-5-thia-1-azabicyclo[4.2.0]oct-2-ene-2-carboxylic acid, and 3-[[[(6R,7R)-7-[(Z)-2-(2-amino-4-thiazolyl)-2-[[[(3,4-dihydroxyphenyl)sulphonyl]methoxy]imino]acetamido]-2-carboxy-8-oxo-5-thia-1-azabicyclo[4.2.0]oct-2-ene-3-yl]methyl]thio]-1-(carbamoylmethyl)pyridinium betaine.

The compounds of formula 1 form pharmaceutically acceptable salts with bases. Examples of salts of compounds of formula I are the alkali metal salts, for example, the sodium and potassium salts, the ammonium salts, the alkaline earth metal salts, for example, calcium salts, the salts with organic bases, for example, with amines such as diisopropylamine, benzylamine, N,N-dibenzyl-amine, triethanolamine, triethylamine, N,N-dibenzyl-ethylenediamine, N-methylmorpholine, pyridine, piperazine, N-ethylpiperidine, N-methyl-D-glucamine and procaine or with amino acids such as arginine and lysine. Mono-, di-, and tri-salts can result, depending on the number of acidic groups in the compounds of formula I.

The compounds of formula I, which have a basic substituent, also form internal salts and acid addition salts with organic and inorganic acids. Examples of acid addition salts of compounds of formula I are salts with mineral acids, for example. hydrohalic acids such as hydrochloric acid, hydrogen bromide and hydrogen iodide, sulphuric acid, nitric acid phosphoric acid and the like, salts with organic sulphonic acids, for example, with alkyl- and arylsulphonic acids such as ethanesulphonic acid, p-toluenesulphonic acid, benzenesulphonic acid, and the like, as well as salts with organic carboxylic acids, for example, with acetic acid, tartaric acid, maleic acid, citric acid, benzoic acid, salicyclic acid, ascorbic acid, and the like.

The pharmaceutically acceptable salts can be prepared according to conventional methods known to those skilled in the art.

The readily hydrolyzable esters of the compounds of formula I are, preferably, esters which can be hydrolyzed under mild conditions, especially those which can be hydrolyzed under physiological conditions, for example, enzymatically. Examples of such esters are the 1-(lower alkanoyloxy)-lower alkyl esters, e.g., the acetoxymethyl, pivaloyloxymethyl, 1-acetoxyethyl and the 1-pivaloyloxyethyl esters, the 1-(lower alkoxycarbonyloxy) lower alkyl esters, e.g., the (methoxycarbonyloxy)methyl, 1-(ethoxycarbonyloxy)ethyl and the 1-(isopropoxycarbonyloxy)ethyl esters, the lactonyl esters, e.g., the phthalidyl and thiophthalidyl esters, the 1-(lower alkoxy)-lower alkyl esters, e.g., the methoxymethyl esters, the 1-(lower alkanoylamino)-lower alkyl esters, e.g., the acetamidomethyl esters, the benzyl esters, the cyanomethyl esters, and the (2-oxo-1,3-dioxol-4-yl)methyl esters.

Additional carboxy groups which may be present in a compound of formula I can also be present in the form of readily hydrolyzable ester groups. These readily hydrolyzable esters of the compounds of formula I can be prepared according to procedures which are familiar to those skilled in the art.

The compounds of this invention can be hydrated. Such hydrates can be obtained in situ during the course of the manufacturing process or as a consequence of hygroscopic properties of an initially anhydrous product. Alternatively, a wholly or partially anhydrous product can be exposed to a moist atmosphere.

Compounds in accordance with the invention, i.e., the compounds of formula I above, their readily hydrolyzable esters and pharmaceutically acceptable salts as well as the hydrates of these compounds, esters and salts, can be prepared by the following procedures:

a) acylating a compound of the formula

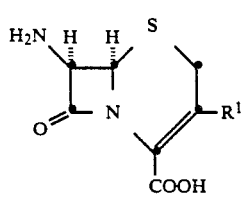

II wherein $R^1$ is as defined above,
or a readily hydrolyzable ester thereof or an acid addition salt of one of these compounds with a compound of the formula

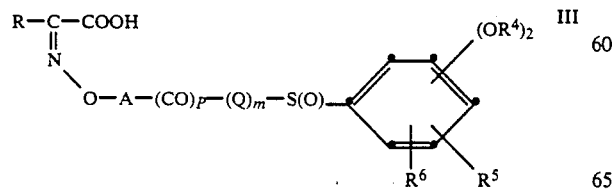

III wherein R, $R^4$, $R^5$, $R^6$, A, Q, m, n and p have the above meanings, or b) reacting a compound of the formula

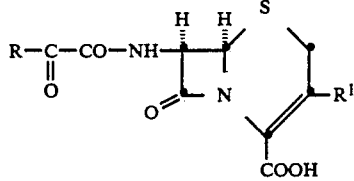

IV wherein R and $R^1$ have the above meanings,
or a readily hydrolyzable ester thereof, optionally in the presence of a copper salt, with a compound of the formula

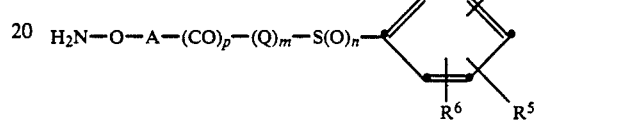

V wherein $R^4$, $R^5$, $R^6$, A, Q, m, n and p have the above meanings,
or with an acid addition salt thereof, or c) alkylating a compound of the formula

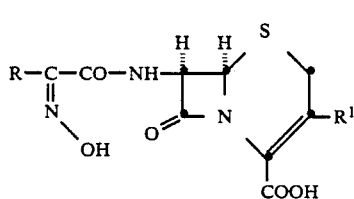

VI wherein R and $R^1$ have the above meanings
or a readily hydrolyzable ester thereof with a compound of the formula

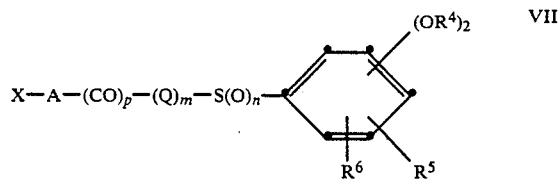

VII wherein X represents a leaving group and $R^4$, $R^5$, $R^6$, A, Q, m, n and p have the above meanings, or d) reacting a compound of the formula

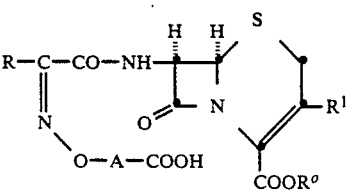

VIII wherein $R^o$ represents a group which is removable by hydrolysis and R, $R^1$ and A have the above meanings,
with a compound of the formula

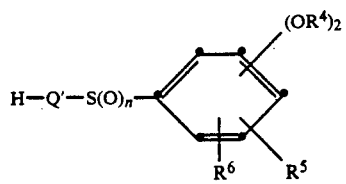

wherein Q' represents the group —NR²— or —NR²NR³— and R², R³, R⁴, R⁵, R⁶ and n have the above meanings, or e) reacting a compound of the formula

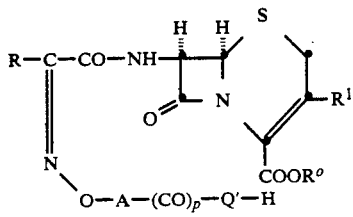

wherein R⁰, R, R¹, A, Q' and p have the above meanings, with a reactive derivative of a sulphonic acid of the formula

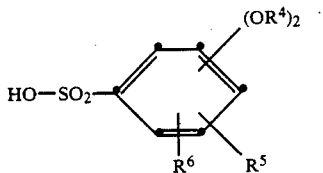

wherein R⁴, R⁵ and R⁶ have the above meanings, or f) reacting a compound of the formula

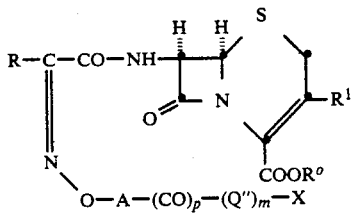

wherein Q" represents lower alkylene or C₃₋₇ cycloalkylene which is optionally substituted with carboxy, carbamoyl lower alkylcarbamoyl or di(-lower alkyl)carbamoyl and R⁰, R, R¹ A, p, m and X have the above meanings, either in the presence of a base with a sulphinic acid or a mercaptan of the formula

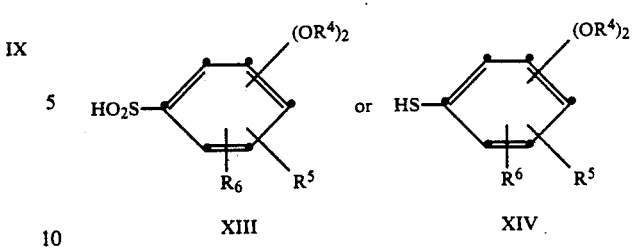

wherein R⁴, R⁵ and R⁶ have the above meanings, or with a salt thereof, or g) reacting a compound of the formula

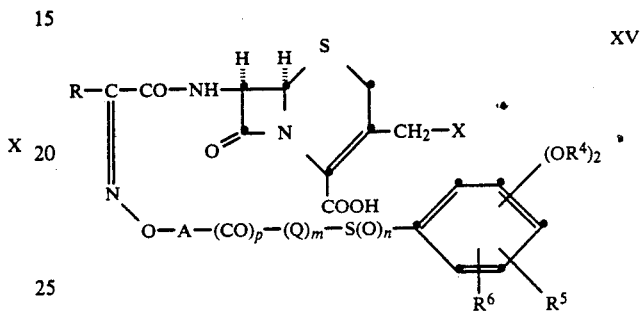

wherein R, R⁴, R⁵, R⁶, A, Q, X, m, n and p have the above meanings, or a readily hydrolyzable ester thereof with a compound of the formula

HS—R"    XVI wherein R" is a heterocyclic group which is attached via a carbon atom, or h) if desired, hydrolyzing a readily hydrolyzable ester of a compound of formula I and i) if desired, converting a product thus obtained into a pharmaceutically acceptable salt or a hydrate.

In the above processes, any reactive amino, hydroxyl or carboxy groups which may be present must be blocked by protecting groups. These instances are readily recognizable by those skilled in the art and, also, the selection of suitable protecting groups will be apparent to him.

Further, it is possible that products in accordance with the invention occur as mixtures with the corresponding isomeric products. Thus, for example, one can obtain oximes having the [E]-configuration or Δ²-isomers of cephalosporin derivatives in accordance with the invention. The separation of these byproducts as well as their recycling to products in accordance with the invention can be effected according to methods which are known to those skilled in the art, for example, using chromatographic and crystallization methods.

Acylation in accordance with process variant (a) can be carried out according to known methods. For example, the compound of formula II can be acylated using the free carboxylic acid of formula III or a salt thereof with a base, with acylation being carried out in the presence of a suitable condensation agent and the compound of formula II being first converted into a readily hydrolyzable ester. Suitable condensation agents are, for example, N,N'-disubstituted carbodiimides such as N,N'-dicyclohexylcarbodiimide which are preferably used together with N-hydroxybenzotriazole or N-hydroxysuccinimide, 2-halopyridinium salts such as 2-chloro-1-methylpyridinium chloride, phosphorus oxychloride, thionyl chloride and oxalyl chloride.

It is also possible to use the carboxylic acid of formula III in the form of a reactive derivative. Suitable reactive derivatives include acid chlorides, acid anhydrides mixed anhydrides (for example, anhydrides with trifluoroacetic acid, benzenesulphonic acid, mesitylenesulphonic acid, p-toluenesulphonic acid and p-chlorosulphonic acid) and active thiol esters, for example, S-(2-benzothiazolyl)-thioesters.

If desired, the acylation can be carried out in the presence of an acid-binding agent, such as sodium hydrogen carbonate, potassium carbonate, triethylamine, pyridine or N-methylmorpholine. Suitable solvents are, for example, cyclic ethers such as tetrahydrofuran and dioxan, halogenated lower hydrocarbons such as chloroform and methylene chloride, dimethylformamide, dimethylacetamide, acetonitrile, acetone and water, as well as mixtures thereof. The reaction temperature can vary within a wide range, typically between $-50°$ C. and $50°$ C., and preferably between about $-10°$ C. and $30°$ C.

Oxime formation in accordance with process variant (b) can also be carried out according to known methods. The compound of formula V is preferably used in the form of an acid addition salt, for example, as the hydrochloride or as the p-toluenesulphonate. Suitable solvents are, for example, water, lower alcohols such as methanol, cyclic ethers such as tetrahydrofuran and dioxan, acetonitrile, dimethylformamide and dimethylacetamide, as well as mixtures thereof. In a preferred embodiment, dimethylacetamide is used as the solvent. In a further preferred embodiment the reaction is carried out in the presence of a copper salt, with both copper(I) salts and copper(II) salts being suitable. Suitable salts are, for example, the corresponding halides, e.g., chlorides and bromides, sulphates, acetates, nitrates, oxides, carbonates, perchlorates and the tetrafluoroborates. The reaction temperature is in the range from $-20°$ C. to $40°$ C. preferably $0°$ C. to $30°$ C.

Alkylation in accordance with process variant (c) can also be carried out according to known methods. For example, the compounds of formulae VI and VII can be reacted with one another in the presence of an inorganic or organic base and in an inert organic solvent, preferably in an aprotic solvent. Suitable bases are, for example, potassium carbonate, sodium hydride or tertiary amines such as triethylamine. Suitable solvents are dimethylformamide, dimethylacetamide, dimethyl sulphoxide and acetone, as well as mixtures thereof.

It is, however, also possible to convert the oxime of formula VI with a strong base, such as sodium or lithium hydride, into the corresponding sodium or lithium salt and then to react this with the compound of formula VII. The solvents mentioned above are also suitable for this procedure.

The leaving group denoted by X is preferably a halogen atom, for example, a chlorine, bromine or iodine atom, or an arylsulphonyloxy group, for example, the p-toluene-sulphonyloxy group. The reaction is usually carried out at temperatures between $-70°$ C. and $60°$ C., preferably between $-20°$ C. and $20°$ C.

Readily hydrolyzable esters of the compounds of formula I in which p and m are the number 1. Q is the group $-NR^2-$ or $-NR^2NR^3-$, and $R^2$ and $R^3$ and the remaining substituents have the same meanings as above can be prepared in accordance with process variant (d). This process can also be carried out according to known methods. For example, the same reaction conditions as given above for process variant (a) can be used.

Readily hydrolyzable esters of the compounds of formula I in which m is 1, n is 2 and Q is the group $-NR^2-$ or $-NR^2NR^3-$, and $R^2$, $R^3$ and the remaining substituents have the same meanings as above can be prepared in accordance with variant (e). This process can also be carried out according to known methods. A sulphonic acid halide, especially a sulphonic acid chloride, is preferably used as the reactive sulphonic acid derivative. The reaction is preferably carried out in the presence of a base, e.g., a tertiary amine such as triethylamine. Suitable solvents are, for example, cyclic ethers such as tetrahydrofuran and dioxan open-chain ethers such as diethyl ether, halogenated lower hydrocarbons such as chloroform and methylene chloride, dimethylformamide, dimethylacetamide, acetonitrile and acetone. The reaction can be carried out at a temperature in the range from $-50°$ C. to $50°$ C., preferably between $-10°$ C. and $30°$ C.

Readily hydrolyzable esters of compounds of formula I in which Q is lower alkylene or $C_{3-7}$-cyclo-alkylene which is optionally substituted with carboxy, carbamoyl, lower alkylcarbamoyl or di(lower alkyl)-carbamoyl and n is zero or 1 and the remaining substituents have the above meanings, can be prepared in accordance with variant (f). This process can also be carried out according to methods which are known. For instance, the reaction can be carried out in an inert solvent, for example, a halogenated lower hydrocarbon such as methylene chloride and chloroform, in a cyclic ether such as tetrahydrofuran or dioxan, in an open-chain ether such as diethyl ether, in dimethylformamide, dimethylacetamide, dimethyl sulphoxide or in acetone, in the presence of a base such as potassium carbonate or a tertiary amine such as triethylamine. It is, however, also possible to use the sulphinic acid of formula XIII or the mercaptan of formula XIV in the form of a salt, with the lithium, sodium and potassium salts being especially preferred for this purpose. The reaction can be carried out over a wide temperature range, but preferably at room temperature.

Compounds of formula I in which $R^1$ is the group $-CH_2-S-R''$ and $R''$ is a heterocyclic group attached via a carbon atom and the remaining symbols have the above meanings can be prepared in accordance with variant (g). This process can also be carried out according to methods which are known. The leaving group denoted by X is preferably a halogen atom, e.g., chlorine, bromine or iodine, a lower alkyl- or arylsulphonyloxy group such as methanesulphonyloxy or p-toluenesulphonyloxy, or a lower alkanoyloxy group such as acetoxy. The symbol X preferably signifies acetoxy. The reaction can be carried out, for example, under the same conditions as are described above for process variant (f).

For the preparation of the readily hydrolyzable esters of the carboxylic acids of formula I in accordance with variant (h), the carboxylic acid is preferably reacted with the corresponding halide containing the ester group, preferably with the iodide. The reaction can be accelerated with the aid of a base, e.g., an alkali metal hydroxide or carbonate, or an organic amine such as triethylamine. This reaction is preferably carried out in an inert organic solvent such as dimethylacetamide hexamethylphosphoric acid triamide dimethyl sulphoxide or, preferably, dimethylformamide. The temperature preferably lies in the range from about $0°$ to $40°$ C.

The preparation of the salts and hydrates of the compounds of formula I and, respectively, of the hydrates of these salts in accordance with variant (i) can be effected in a manner known per se, e.g., by reacting the carboxylic acid of formula I or a salt thereof with an equivalent amount of the desired base, conveniently in a solvent such as water or in an organic solvent such as ethanol, methanol, acetone or many others. Correspondingly, salt formation is brought about by the addition of an organic or inorganic acid. The temperature of the salt formation is not critical. In general it is at room temperature, but it can also be slightly over or under, for example, in the range from 0° C. to +50° C.

The preparation of the hydrates occurs for the most part in situ during the course of the manufacturing process or as a consequence of the hygroscopic properties of an initially anhydrous product. Alternatively, a completely or partially anhydrous product (carboxylic acid of formula I or ester or salt thereof) can be exposed to a moist atmosphere, e.g., at about +10° C. to +40° C.

The various compounds which are used as starting materials are known or can be prepared according to known methods and starting from known starting materials. The Examples below contain detailed information concerning the preparation of starting materials.

As already mentioned, the compounds in accordance with the invention are useful as antibiotics, and they possess a broad spectrum of activity against both Gram-positive and Gram-negative microorganisms.

To illustrate the antimicrobial activity of compounds in accordance with the invention, various compounds prepared in accordance with the working Examples hereinafter were tested for their activity in vitro. The activities (Minimum Inhibitory Concentration in µg/ml) ascertained are compiled in the following Table:

enteral or parenteral administration. These compounds can be administered, for example, perorally, such as in the form of tablets, coated tablets, dragees, hard and soft gelatine capsules, solutions, emulsions or suspensions; rectally, such as in the form of suppositories; or parenterally, such as in the form of injection solutions.

The preparation of such pharmaceutical dosage forms can be effected using conventional techniques familiar to those skilled in the art by combining the antibacterial compound with suitable, non-toxic inert therapeutically compatible solid or liquid carrier materials and, if desired, the usual pharmaceutical adjuvants.

As such carrier materials there are suitable not only inorganic carrier materials, but also organic carrier materials. Thus, there can be used as carrier materials for tablets, coated tablets, dragees and hard gelatine capsules materials such as, for example, lactose, maize starch or derivatives thereof, talc, stearic acid or its salts. Suitable carriers for soft gelatine capsules are, for example, vegetable oils, waxes, fats and semi-solid and liquid polyols (depending on the nature of the active substance; no carriers are, however, required in the case soft gelatine capsules). Suitable carrier materials for the preparation of solutions and syrups are, for example, water, polyols, saccharose, invert sugar and glucose. Suitable carrier materials for injection solutions are, for example, water, alcohols, polyols, glycerine and vegetable oils. Suitable carrier materials for suppositories are, for example, natural or hardened oils, waxes, fats and semi-liquid or liquid polyols.

As pharmaceutical adjuvants there come into consideration the usual preservatives, solubilizers, stabilizers, wetting agents, emulsifiers, sweeteners, colorants, flavorants, salts for varying the osmotic pressure, buffers, coating agents and antioxidants.

The compounds of formula I and their salts and,

TABLE I

| Organism | End product from Example | | | | | | | | |
|---|---|---|---|---|---|---|---|---|---|
| | 1 | 2 | 3 | 5 | 6 | 7 | 8 | 9 | 10 |
| E. coli 25922 | <0.06 | <0.06 | <0.06 | <0.06 | <0.06 | <0.06 | <0.06 | <0.06 | 0.12 |
| E. coli TEM 1 | <0.06 | <0.06 | <0.06 | <0.06 | <0.06 | <0.06 | <0.06 | <0.06 | <0.06 |
| K. pneumoniae 418 | <0.06 | <0.06 | <0.06 | <0.06 | <0.06 | <0.06 | <0.06 | <0.06 | <0.06 |
| K. oxytoca 1082 E | 0.25 | 0.12 | <0.06 | <0.06 | 1 | <0.06 | 0.12 | 0.12 | 0.12 |
| E. cloacae 15 M | 0.12 | 0.12 | 0.25 | <0.06 | <0.06 | <0.06 | — | 0.5 | 1 |
| S. marcescens 80315 | 0.12 | <0.06 | <0.06 | <0.06 | 0.12 | <0.06 | <0.06 | 0.12 | 0.25 |
| P. mirabilis 2117 | 0.12 | 0.12 | 0.12 | <0.06 | <0.06 | 0.12 | 0.12 | 0.25 | 0.12 |
| P. vulgaris 1028 | 0.12 | 0.12 | 0.12 | <0.06 | 0.25 | 0.12 | <0.06 | 0.12 | 0.25 |
| P. aeruginosa BA | 0.25 | 0.25 | 0.25 | 0.12 | 1 | 0.25 | 0.25 | 1 | 0.5 |
| S. pyogenes B15 | 0.25 | 0.25 | 0.25 | 1 | 2 | 0.5 | 0.25 | 0.5 | 2 |
| M. morganii 6H-1371 | 0.25 | 0.25 | 1 | 0.25 | <0.06 | 0.5 | <0.06 | 0.25 | 0.5 |
| C. freundii 902 | 0.25 | 0.25 | 0.25 | 0.12 | 0.12 | 0.12 | <0.06 | 0.25 | 0.25 |

TABLE II

| Organism | End product from Example | |
|---|---|---|
| | 7 | 15 |
| E. coli 25922 | 0.12 | <0.06 |
| E. coli TEM 1 | <0.06 | <0.06 |
| K. pneumoniae 418 | <0.06 | <0.06 |
| K. oxytoca 1082 E | 0.25 | 0.5 |
| E. cloacae 15 M | 0.5 | 0.5 |
| S. marcescens 80315 | <0.06 | <0.06 |
| P. mirabilis 2117 | 0.25 | 0.12 |
| P. vulgaris 1028 | 0.25 | 0.12 |
| P. aeruginosa BA | 0.25 | 0.12 |
| S. pyogenes B15 | 0.5 | 0.5 |
| M. morganii 6H-1371 | 0.5 | 0.25 |
| C. freundii 902 | 0.25 | 0.12 |

< means less than

The compounds in accordance with the invention can be used in the form of pharmaceutical preparations for respectively, hydrates are especially useful for parenteral application and for this purpose are preferably provided as lyophilizates or dry powders for dilution with usual carriers such as water or isotonic saline. The readily hydrolyzable esters of compounds of formula I and their salts and hydrates are especially useful for enteral application.

The pharmaceutical compositions can contain the antibacterial compounds in accordance with the invention in therapeutically effective amounts of about 25-2000 mg, preferably 100-1000 mg, per unit dosage form. For adults, a daily dosage of about 0.05 g to about 4 g, especially about 0.1 g to about 2 g, is usually appropriate.

The following Examples are intended to illustrate the present invention in more detail, but are not intended to limit its scope in any manner. All temperatures are given in degrees Celsius.

EXAMPLE 1

In a first flask, a solution of 74 mg of 2-amino-4-thiazoleglyoxylic acid (Z)-O-[[(3,4-dihydroxyphenyl)-sulphonyl]methyl] oxime in 1 ml of N,N-dimethylformamide was treated with 83 mg of N,O-bis-(trimethylsilyl) acetamide and stirred at 20° C. for 15 minutes. The solution was cooled to 0° C. and treated in succession with 39 mg of 1-hydroxy-benzotriazole and 51 mg of N,N'-dicyclohexylcarbodiimide. The reaction mixture was stirred at 0° C. for 1 hour, whereby a precipitate formed.

In a second flask, 64 mg of (7R)-7-aminocephalosporanic acid and 124 mg of N,O-bis-(trimethylsilyl)acetamide in 1 ml of N,N-dimethylformamide were stirred at 20° C. for 20 minutes. A clear solution was obtained which was added at 0° C. to the solution in the first flask. The reaction mixture was stirred at 0° C. for 1 hour and at 20° C. for 2 hours. The precipitate was filtered off under suction and the filtrate was partitioned between 2% aqueous sodium hydrogen carbon solution and ethyl acetate. The aqueous phase was adjusted to pH 7 with 3N hydrochloric acid, concentrated in a vacuum to a volume of about 5 ml and the concentrated solution was chromatographed on MCI gel CHP2OP (Mitsubishi Chemical Industries Ltd.). Elution was carried out first with 1% aqueous acetic acid and then with mixtures of 1% aqueous acetic acid/methanol, using increasing amounts of methanol. By lyophilization of the product fractions, which were concentrated in a vacuum, there was obtained (6R,7R)-3-(acetoxymethyl-)-7-[(Z)-2-(2-amino-4-thiazolyl)-2-[[[(3,4-dihydroxyphenyl)sulphonyl)]methoxy]imino]acetamido]-8-oxo-5-thia-1azabicyclo[4.2.0]oct-2-ene-2-carboxylic acid as a white powder.

$^1$H NMR (DMSO-d$_6$): δ2.03 (s, 3H); 3.56 (d, J=22 Hz, 1H, signal of the coupling partner overlapped by the H$_2$O signal at 3.45); 4.70 (d, J=12.5 Hz, 1H); 4.99 (d, J=12.5 Hz, 1H); 5.08 (d, J=5 Hz, 1H); 5.17 (d, J=12.5 Hz, 1H); 5.25 (d, J=12.5 Hz, 1H); 5.69 (dd, J=8 and 5 Hz, 1H); 6.72 (s, 1H); 6.90 (d, J=8 Hz, 1H); 7.19 (d, J=1 Hz, 1H); 7.22 (dd, J=8 and 1 Hz, 1H); 7.32 (broad s, 2H); 9.66 (broad d, J=8 Hz, 1H) ppm.

The 2-amino-4-thiazoleglyoxylic acid (Z)-O-[[(3,4-dihydroxyphenyl)sulphonyl]methyl] oxime used as the starting material was prepared as follows:

a) 135 ml of a 1.7M butyllithium/n-hexane solution were added dropwise within 3 minutes to 220 ml of diethyl ether pre-cooled to −40° C. The solution was cooled to −50° C. and then treated within 5 minutes with a solution of 50.4 g of 5-bromo-2,2-dimethyl-1,3-benzodioxol in 100 ml of diethyl ether, upon which the temperature rose to −35° C. The reaction solution was warmed to −10° C. and stirred at this temperature for 30 minutes. Then, 6.6 g of sulphur were introduced in portions into the reaction solution, which had been cooled to −60° C. The temperature then rose to −25° C. The reaction mixture was stirred at 0° C. for a further 15 minutes. 34 g of methyl iodide were then added and the reaction mixture was stirred at 0° C. for 1 hour. The reaction solution was diluted with ethyl acetate and washed in succession with 200 ml of 2N aqueous sodium hydroxide solution and 200 ml of water. The organic phase was dried over sodium sulphate and the solvent was removed in a vacuum. The residual oil was fractionated in a vacuum over a 60 cm long Vigreux column. There was obtained 2,2-di-methyl-5-(methylthio)-1,3-benzodioxol as a colorless oil having a boiling point of 80°–83° C. (20 Pa).

b) A solution of 19.6 g of 2,2-dimethyl-5-(methylthio)-1,3-benzodioxol in 500 ml of methylene chloride was treated at 0° C. with 20.3 g of 85% m-chloroperbenzoic acid. The mixture was subsequently stirred at 0° C. for 1 hour. A white precipitate resulted. The reaction mixture was extracted with 400 ml of 17% aqueous sodium carbonate solution and 400 of water. The organic phase was dried over sodium sulphate and freed from solvent in a vacuum. The residue was taken up in a small amount of methylene chloride and chromatographed on silica gel, with elution being carried out with ethyl acetate/n-hexane/methylene chloride (1:1:1, v/v/v). After crystallization from ethyl acetate/n-hexane, there was obtained 2,2-dimethyl-5-(methyl-sulphinyl)-1,3-benzodioxol as white crystals having a melting point of 87°–88° C.

c) To a solution, cooled to 0° C., of 16.5 g of 2,2-dimethyl-5-(methylsulphinyl)-1,3-benzodioxol and 6.2 g of pyridine in 230 ml of methylene chloride, there were added in succession 5.43 g of bromine and 12.1 g of N-bromosuccin-imide. The reaction mixture was stirred at 0° C. for 3 hours and then at 20° C. for a further 12 hours. The orange colored solution was cooled to 0° C., treated with 40 ml of 1M aqueous sodium sulphite solution and the pH of the mixture was adjusted to 7 by the addition of 17% aqueous sodium carbonate solution. After stirring for 10 minutes, the phases were separated. The organic phase was washed in succession with 50 ml of 1N aqueous hydrochloric acid, 50 ml of 5% sodium hydrogen carbonate solution and 3 times with 100 ml of water each time, dried over sodium sulphate and evaporated in a vacuum. The residue was chromatographed on silica gel, with elution being carried out with ethyl acetate/hexane (1:2, v/v). After crystallization from acetone/water, there was obtained 5-[(bromomethyl)-sulphinyl]-1,3-benzodioxol as white crystals having a melting point of 88°–89° C.

d) A mixture of 8.73 g of 5-[(bromomethyl)sulphinyl]-2,2-dimethyl-1,3-benzodioxol, 6.45 g of (Z)-2-[amino-α-(hydroxyimino)]-4-thiazoleacetic acid ethyl ester and 4.97 g of potassium carbonate in 36 ml of dimethyl sulphoxide was stirred at 75° C. for 2 hours. After cooling, the reaction mixture was diluted with 100 ml of ethyl acetate and extracted 4 times with 50 ml of 5% aqueous sodium chloride solution each time. The organic phase was dried over sodium sulphate and freed from solvent in a vacuum. The residue was taken up in 60 ml of methylene chloride. Undissolved material was separated by filtration and the filtrate was treated at 20° C. with 9.4 g of 55% m-chloroperbenzoic acid. The reaction mixture was stirred at 20° C. for 1 hour, then diluted with methylene chloride and washed in succession with 17% aqueous sodium carbonate solution and water. The organic phase was dried over sodium sulphate and freed from solvent in a vacuum. The residue was chromatographed on silica gel. A mixture of ethyl acetate/n-hexane (1:1, v/v) eluted the product, which was crystallized from ethyl acetate/n-hexane. There was obtained 2-amino-4-thiazoleglyoxylic acid ethyl ester (Z)-(O)-[[[(3,4-(isopropylidenedioxy)phenyl]sulphonyl]methyl] oxime as white crystals having a melting point of 160°–161° C.

e) A solution of 441 mg of 2-amino-4-thiazoleglyoxylic acid ethyl ester (Z)-O-[[[(3,4-(isopropylidenedioxy)-phenyl]sulphonyl]methyl] oxime in 5M ethanolic hydrochloric acid was heated to 80° C. for 3 hours. The reaction solution was suction filtered and the solvent was removed in a vacuum. The residue was taken up in 2 ml of ethanol and 2 ml of 2N aqueous sodium hydroxide solution. The dark solution obtained was stirred at 20° C. for 30 minutes. 4 ml of water were then added and the pH was adjusted to 7 with 3N aqueous hydrochloric acid. The solution was concentrated to about 3 ml in a vacuum and then chromatographed on MCI gel CHP2OP. Elution was carried out first with 2% aqueous acetic acid, then with water/methanol mixtures, using greater and greater amounts of methanol. The product was eluted with water/methanol (9:1, v/v) and then crystallized from methanol/diethyl ether. There was thus obtained 2-amino-4-thiazoleglyoxylic acid (Z)-O-[[(3,4-dihydroxyphenyl)sulphonyl]methyl] oxime as white crystals having a melting point of 167° C. (dec.).

$^1$NMR (DMSO-$d_6$): δ5.24 (s, 2H); 6.73 (s, 1H); 6.88 (d, J=8 Hz, 1H); 7.19 (dd, J=8 and 1 Hz, 1H); 7.23 (d, J=1 Hz, 1H); 7.26 (s, 2H); 9.79 (broad s, 1H); 10.15 (broad s, 1H) ppm.

EXAMPLE 2

The procedure of Example 1 was repeated, but substituting for the (7R)-7-aminocephalosporanic acid an equimolar amount of (6R,7R)-7-amino-3-[[(5-methyl-1,3,4-thiadiazol-2-yl)thio]methyl]-8-oxo-5-thia-1-azabicyclo[4.2.0]oct-2-ene-2-carboxylic acid. There was obtained, after chromatographic purification on MCI gel and lyophilization of the product fractions. (6R,7R)-7-[(Z)-2-(amino-4-thiazolyl)-2-[[[(3,4-dihydroxyphenyl)sulphonyl]methoxy]imino]acetamido]-3-[[(5-methyl-1,3,4-thiadiazol-2yl)thio]methyl]-8-oxo-5-thia-1-azabicyclo[4.2.0]oct-2-ene-2-carboxylic acid as a white powder.

$^1$H NMR (DMSO-$d_6$): δ2.68 (s, 3H); 3.44 (d, J=19 Hz, 1H); 3.66 (d, J=19 Hz, 1H); 4.20 (d, J=13 Hz, 1H); 4.52 (d, J=13 Hz, 1H); 5.06 (d, J=5 Hz, 1H); 5.14 (d, J=12.5 Hz, 1H); 5.21 (d, J=12.5 Hz, 1H); 5.64 (dd, J=8 and 5 Hz, 1H); 4.89 (d, J=8 Hz, 1H); 7.19 (d, J=1 Hz, 1H); 7.12 (dd, J=8 and 1 Hz, 1H); 7.30 (s, 2H) ppm.

EXAMPLE 3

The procedure of Example 1 was repeated, but substituting for the (7R)-7-aminocephalosporanic acid an equimolar amount of (6R,7R)-7-amino-3-(azidomethyl)-8-oxo-5-thia-1-azabicyclo-[4.2.0]oct-2-ene-2-carboxylic acid. There was thus obtained, after chromatographic purification on MCI gel and lyophilization of the product fractions, (6R,7R)-7-[(Z)-2-(amino-4-thiazolyl)-2-[[[(3,4-dihydroxyphenyl)sulphonyl]-methoxy]imino]acetamido]-3-(azidomethyl)-8-oxo-5-thia-1-azabicyclo[4.2.0]oct-2-ene-2-carboxylic acid as a white powder.

$^1$H NMR (DMSO-$d_6$): δ3.45 (d, J=19 Hz, 1H); 3.61 (d, J=19 Hz, 1H); 3.91 (d, J=14 Hz, 1H); 4.36 (d, J=14 Hz, 1H); 5.10 (d, J=5 Hz, 1H); 5.16 (d, J=13 Hz, 1H); 5.24 (d, J=13 Hz, 1H); 5.76 (dd, J=8 and 5 Hz, 1Hz); 6.69 (s, 1H); 6.92 (d, J=9 Hz, 1H); 7.20 (m, 2H); 7.31 (s, 2H); 9.69 (s, 1H); 9.76 (d, J=8 Hz, 1H); 10.12 (s, 1H) ppm.

EXAMPLE 4

The procedure of Example 1 was repeated, but substituting for the (7R)-7-aminocephalosporanic acid an equimolar amount of 1-[[[(6R,7R)-7-amino-2-carboxy-8-oxo-5-thia-1-azabicyclo-[4.2.0]oct-2-ene-3-yl]methyl]-pyridinium betaine hydrochloride. There was obtained after chromatographic purification on MCI gel and lyophilization of the product fractions, 1-[(6R,7R)-7-[(Z)-2-(2-amino-4-thiazolyl)-2-[[[(3,4-dihydroxyphenyl)sulphonyl]methoxy]imino]acetamido]-2-carboxy-8-oxo-5-thia-1-azabicyclo[4.2.0]oct-2-ene-3-yl]pyridinium betaine as a white powder.

$^1$H NMR (DMSO-$d_6$): δ inter alia 2.97 (d, J=18 Hz, 1H); 3.46 (d. J=18 Hz, 1H); 6.67 (s, 1H); 6.89 (d, J=8 Hz, 1H); 7.18 (m, 2H); 7.29 (broad s, 2H) ppm.

EXAMPLE 5

In a first flask, a solution of 52 mg of 2-amino-4-thiazoleglyoxylic acid (Z)-O-[[[(3,4-dihydroxyphenyl)-sulphonyl]methyl] oxime in 0.7 ml of N,N-dimethylformamide was cooled to 0° C. and treated with 27 mg of 1-hydroxybenzotriazole and 36 mg of N,N'-dicyclohexylcarbodiimide. The reaction mixture was stirred at 0° C. for 1 hour, upon which a precipitate formed.

In a second flask 74 mg of (6R 7R)-7-amino-3-[[(2-carboxy-5-methyl-s-triazolo[1,5-a]pyrimidin-7-yl)thio]methyl]-8-oxo-5-thia-1-azabicyclo[4.2.0]oct-2-ene-2-carboxylic acid and 86 mg of N,O-bis(trimethylsilyl)acetamide in 0.7 ml of N,N-dimethylformamide were stirred at 20° C. for 30 minutes. There resulted a clear solution which was added at 0° C. to the solution in the first flask. The reaction mixture was stirred at 20° C. for 2 hours and then partitioned between ethyl acetate and 2% aqueous sodium hydrogen carbonate solution. The aqueous phase was adjusted to pH 7 with 3N aqueous hydrochloric acid, concentrated in a vacuum to a volume of about 5 ml, and the concentrated solution was chromatographed on MCI gel CHP2OP. Elution was carried out first with 1% acetic acid and later with mixtures of 1% aqueous acetic acid/methanol, using increasing amounts of methanol. By lyophilization of the product fractions, which had been concentrated in a vacuum, there was obtained (6R,7R)-7-[(Z)-(2-amino-4-thiazolyl)-2-[[[(3,4-dihydroxyphenyl)sulphonyl]-methoxy]imino]acetamido]-3-[[(2-carboxy-5-methyl-s-triazolo[1,5-a]pyrimidin-7-yl)thio]methyl]-8-oxo-5-thia-1-azabicyclo[4.2.0]oct-2-ene-2-carboxylic acid as a white powder.

$^1$H NMR (DMSO-$d_6$): δ2.62 (s, 3H); 3.53 (d, J=19 Hz, 1H); 3.74 (d, J=19 Hz, 1H); 4.38 (d, J=13 Hz, 1H); 4.47 (d, J=13 Hz, 1H); 5.12 (d, J=5 Hz, 1H); 5.15 (d, J=12 Hz, 1H); 5.23 (d, J=12 Hz, 1H); 5.75 (dd, J=8 and 5 Hz, 1H); 6.69 (s, 1H); 6.92 (d, J=9 Hz, 1H); 7.20 (m, 2H); 7.30 (broad s, 2H); 7.45 (s, 1H); 9.68 (broad s, 1H); 9.72 (d, J=8 Hz, 1H): 10.14 (broad s, 1H) ppm.

EXAMPLE 6

37 mg of 2-amino-4-thiazoleglyoxylic acid (Z)-O-[[(3,4-dihydroxyphenyl)-sulphonyl]methyl] oxime were reacted with 47 mg of (6R,7R)-7-amino-3-[[(2,5-dihydro-6-hydroxy-2-methyl -5-oxo-as-triazin-3-yl)thio]methyl]-8-oxo-5-thia-1-azabicyclo[4.2.0]oct-2-ene-2-carboxylic acid according to the procedure described in Example 5. The product fractions obtained upon chromatography on MCI gel according to the method described in Example 1 were concentrated and the pH of solution thus obtained was adjusted to 7 with dilute sodium hydroxide solution. By lyophilization, there was obtained (6R,7R)-7-[(Z)-2-(2-amino-4-thiazolyl)-2-[[[(3,4-dihydroxyphenyl)sulphonyl]methoxy]imino]acetamido]-3-[[(2,5-dihydro-6-hydroxy-2-methyl-5-oxo-as-triazin-3-yl)thio]methyl]-8-oxo-5-thia- 1-azabicyclo[4.2.0]oct-2-ene-2-carboxylic acid disodium salt as a pale yellow powder.

$^1$H NMR (DMSO-d$_6$): δ inter alia 4.91 (d, J=5 Hz, 1H); 5.09 (d, J=13 Hz, 1H); 5.19 (d, J=13 Hz, 1H): 5.43 (m, 1H); 6.77 (s, 1H) ppm.

EXAMPLE 7

48 mg of 4-[[(aminooxy)methyl]sulphonyl]pyrocatechol were dissolved in 2 ml of 1N ethanolic hydrochloric acid and the solution was concentrated completely in a vacuum. The residue was dissolved in 3 ml of ethanol and the solvent was removed completely in a vacuum. The crude hydrochloride was dissolved in 0.5 ml of N,N-dimethylacetamide together with 90 mg of (6R,7R)-7-(2-amino-4-thiazoleglyoxylamido)-3-[[(2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid and the solution was stirred at room temperature for 64 hours. The reaction solution was treated slowly at 20° C. with 5 ml of water. A precipitate formed, which was filtered off under suction. For purification, the crude product was dissolved in 3 ml of water by the addition of a small amount of 1N sodium hydroxide solution and then chromatographed on MCI gel CHP2OP (Mitsubishi Chemical Industries, Ltd.). Elution was carried out first with 1% aqueous acetic acid and then with mixtures of 1% aqueous acetic acid/methanol using increasing amounts of methanol. By concentration and lyophilization of the product fractions, there was obtained (6R,7R)-7-[(Z)-2-(2-amino-4-thiazolyl)-2-[[[(3,4-di-hydroxyphenyl)sulphonyl]methoxy]imino]acetamido]-3-[[(2-carbamoyl-5-methyl-s-triazolo[1,5-a]pyrimidin-7-yl)-thio]methyl]-8-oxo-5-thia-1azabicyclo[4.2.0]oct-2-ene-2-carboxylic acid as a white powder.

$^1$H NMR (DMSO-d$_6$) δ2.61 (s, 3H), 3.50 (d, J=18 Hz, 1H): 3.77 (d, J =18 Hz, 1H); 4.38 (d, J=14 Hz, 1H); 4.43 (d, J=14 Hz, 1H); 5.14 (d, J=5 Hz, 1H); 5.16 (d, J=14 Hz, 1H): 5.24 (d, J=14 Hz, 1H): 5.74 (dd J=8 and 5 Hz 1H); 6.69 (s, 1H); 6.91 (d, J=8 Hz, 1H); 7.20 (m, 2H); 7.29 (broad s, 2H); 7.41 (s, 3H); 7.88 (s, 1H); 8.17 (s, 1H); 9.67 (s, 1H); 9.72 (d. J=8 Hz, 1H); 10.12 (s, 1H) ppm.

A suspension of 373 mg of (6R,7R)-7-[(Z)-2-(2-amino-4-thiazolyl)-2-[[[(3,4-dihydroxyphenyl)sulphonyl]methoxy]imino]acetamido]-3-[[(2-carbamoyl-5-methyl-s-triazolo[1,5-a]pyrimidin-7-yl)-thio]methyl]-8-oxo-5-thia-1-azabicyclo[4.2.0]oct-2-ene-2-carboxylic acid in 7 ml of water was treated portionwise while stirring with 91 mg of N-methyl-D-glucamine. The resulting clear solution was lyophilized. There was obtained (6R,7R)-7-[(Z)-2-(2-amino-4-thiazolyl)-2-[[[(3,4-di-hydroxyphenyl)sulphonyl]methoxy]imino]acetamido]-3-[[(2-carbamoyl-5-methyl-s-triazolo[1,5-a]pyrimidin-7-yl)-thio]methyl]-8-oxo-5-thia-1-azabicyclo[4.2.0]oct-2-ene-2-carboxylic acid N-methyl-D-glucamine salt as a white powder.

$^1$H NMR (DMSO-d$_6$): δ2.54 (s, 3H); 2.59 (s, 3H); 2.7-4.0 (m, about 20H); 4.34 (d, J=14 Hz, 1H); 4.56 (d, J=14 Hz, 1H); 4.94 (d, J=5 Hz, 1H); 5.12 (d, J=14 Hz, 1H); 5.20 (d, J=14 Hz, 1H); 5.45 (dd, J=8 and 5 Hz, 1H); 6.75 (s, 1H); 6.86 (d, J=8 Hz, 1H); 7.15 (d, J=1 Hz, 1H); 7.2-7.4 (m, 3H); 7.72 (s, 1H); 7.82 (s, 1H); 8.17 (s, 1H); 9.45 (d, J=8 Hz, 1H) ppm.

The 4-[[(aminooxy)methyl]sulphonyl]pyrocatechol used as the starting material in the above procedure was prepared as follows:

a) A mixture of 29.1 g of 5-[(bromomethyl)sulphinyl]-2,2-dimethyl-1,3-benzodioxol, 19.6 g of N-hydroxyphthalimide and 16.7 g of potassium carbonate in 120 ml of dimethyl sulphoxide was stirred at 75° C. for 2 hours. After cooling the reaction mixture was diluted with 400 ml of ethyl acetate and extracted 4 times with 200 ml of 5% sodium chloride solution each time. The organic phase was dried over sodium sulphate and freed from solvent in a vacuum. The residue was dissolved in 200 ml of methylene chloride and treated with 32 g of 55% m-chloroperbenzoic acid while cooling in an ice bath. The reaction mixture was stirred at 20° C. for 1 hour, then diluted with methylene chloride and washed in succession with 17% aqueous sodium carbonate solution and water. The organic phase was dried over sodium sulphate, the solvent was evaporated in a vacuum, and the residual oil was crystallized from methylene chloride/hexane. There was thus obtained N-[[(3,4-isopropylidenedioxy)-phenyl]sulphonyl]methoxy]phthalimide as white crystals having a melting point of 191°-193° C.

b) A suspension of 2.34 g of N-[[(3,4-isopropylidenedioxy)phenyl]sulphonyl]methoxy]phthalimide in 10 ml of ethanol was treated with 0.4 ml of hydrazine hydrate and the mixture was stirred at 20° C. for 45 minutes. There first resulted a clear solution, from which a white precipitate separated later. The reaction mixture was suction filtered, the filtrate was concentrated completely in a vacuum, and the residue was dissolved in 240 ml of 0.6N hydrochloric acid. 200 ml of solvent were distilled off from this solution at room temperature within 3 hours. The concentrated solution was cooled, adjusted to pH 3.5 by the addition of 2N aqueous hydrochloric acid and then chromatographed on MCI gel CHP2OP using 1% aqueous acetic acid as the eluent. The substance fractions were freed from solvent in a vacuum and the residue was triturated with diethyl ether. There was obtained 4-[[(aminooxy)methyl]sulphonyl]pyrocatechol as pale violet crystals having a melting point of 151° C. (dec.).

The (6R,7R)-7-(2-amino-4-thiazoleglyoxylamido)-3-[[(2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid used as the starting compound was prepared as follows:

c) A suspension of 2.50 g of methyl 7-mercapto-5-methyl-s-triazolo[1.5-a]pyrimidine-2-carboxylate (Euro. Pat. Publ. 150,507) in 25ml of 25 percent aqueous ammonia was stirred at room temperature for 6 hours. The mixture was filtered and the solid was dried at 50° in a vacuum. There was obtained 7-mercapto-5-methyl-s-triazolo[1,5-a]pyrimidine-2-carboxamide as a 1:1:1 adduct with water and ammonia.

$^1$H NMR DMSO-d$_6$) δ2.26 (s, 3H); 6.72 (s, 1H); 7.17 (s, 4H, NH$_4$+); 7.60 (broad s, 1H); 7.84 (broad s, 1H) ppm.

d) A mixture of 5.46 g of (7R)-7-aminocephalosporanic acid and 4.85 g of 7-mercapto-5-methyl-s-triazolo[1,5-a]-pyrimidine-2-carboxamide ammonium salt was treated while stirring well with 50 ml of a 20 percent solution of boron trifluoride in acetonitrile. The temperature was kept at below 40° by ice bath-cooling. The reaction mixture was stirred at 20° for 1 hour and subsequently diluted with 200 ml of water. A white precipitate formed, which is collected by filtration. The still-moist material was dissolved in 50 ml of 3N HCl and the solution was filtered. A white product crystallized out from the filtrate after a short time. By filtration, washing with H₂O and acetone and drying in a vacuum, there was obtained (6R,7R)-7-amino-3-[[(2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid as the hydrochloride.

¹H NMR (DMSO-d₆) δ2.61 (s, 3H); 3.74 (d, J=17.5 Hz, 1H); 2.87 (d, J=17.5 Hz, 1H); 4.46 (d, J=12.5 Hz, 1H); 4.54 (d, J=12.5 Hz, 1H); 5.20 (d, J=5 Hz, 1H); 5.25 (d, J=5 Hz, 1H); 7.43 (s, 1H); 7.89 (s, 1H); 8.19 (s, 1H) ppm. MS: 422 (M+H)⁺. IR (KBr): 1770.

e) A suspension of 1.71 g of (6R,7R)-7-amino-3-[[(2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid hydrochloride in 20 ml of methylene chloride was treated with 2.74 ml of N,O-bis-(trimethylsilyl)acetamide. After all had dissolved into solution, 1.32 g of 2-amino-4-thiazolethioglyoxylic acid S-(2-benzothiazolyl) ester were added and the mixture was stirred at 20° for 1.5 hours. Undissolved material was separated by filtration and the filtrate was diluted with 40 ml of methylene chloride. Upon the dropwise addition of 2 ml of ethanol, a yellow precipitate formed, which was collected by filtration and dried in a vacuum. There was obtained (6R,7R)-7-(2-amino-4-thiazoleglyoxylamido)-3-[[(2-carbamoyl-5-methyl-s-triazolo-[1,5-a]pyrimidin-7-yl)thio]methyl]-8-oxo-5-thia-1-azabicyclo[4.2.0]oct-2-ene-2-carboxylic acid as a yellow powder.

¹H NMR (DMSO-d₆): δ2.60 (s, 3H) 3.54 (d, J=17.5 Hz, 1H); 3.74 (d, J=17.5 Hz, 1H); 4.42 (d, J=14 Hz, 1H); 4.56 (d, J=14 Hz, 1H); 5.14 (d, J=5 Hz, 1H); 5.72 (d, J=5 Hz, 1H); 7.41 (s, 2H); 7.55 (s, 1H) ppm.

EXAMPLE 8

(6R,7R)-7-(2-Amino-4-thiazolglyoxylamido)-3 -[[(3-carbamoyl-5-methylpyrazolo[1.5-a]pyrimidin-7-yl)thio]methyl]-8-oxo-5-thia-1-azabicyclo[4.2.0]oct-2-ene-2-carboxylic acid was reacted with 4-[[(aminooxy)methyl]sulphonyl]pyrocatechol according to the procedure described in Example 7. After purification of the crude product using the chromatographic procedure described in Example 7 and lyophilization of the product fractions, there was obtained (6R,7R)-7-[(Z)-2-(2-amino-4-thiazolyl)-2-[[[(3,4-dihydroxyphenyl)sulphonyl]methoxy]imino]acetamido]-3-[[(3-carbamoyl-5-methyl-pyrazolo[1,5-a]pyrimidin-7-yl)thio]-methyl]-8-oxo-5-thia-1-azabicyclo[4.2.0]oct-2-ene-2-carboxylic acid as a white powder.

¹H NMR (DMSO-d₆): δ2.62 (s, 3H); 3.54 (d, J=18 Hz, 1H); 3.75 (d. J=18 Hz. 1H); 4.34 (d, J=13 Hz, 1H); 4.44 (d, J=13 Hz, 1H); 5.15 (d, J=5 Hz, 1H): 5.16 (d, J=14 Hz, 1H); 5.22 (d, J=14 Hz, 1H); 5.74 (dd, J=8 and 5 Hz, 1H); 6.69 (s, 1H); 6.91 (d, J=8 Hz, 1H); 7.18-7.23 (m, 3H); 7.30 (broad s, 2H); 7.49 (broad s, 1H); 7.55 (broad s, 1H); 8.48 (s, 1H); 9.67 (broad s, 1H); 9.73 (d, J=8 Hz, 1H); 10.09 (broad s, 1H) ppm.

The (6R,7R)-7-(2-amino-4-thiazolglyoxylamido)-3-[[(3-carbamoyl-5-methylpyrazolo[1,5-a]pyrimidin-7-yl)thio]methyl]-8-oxo-5-thia-1-azabicyclo[4.2.0]oct-2-ene-2-carboxylic acid used as the starting compound above was prepared as follows:

a) Ethyl 7-mercapto-5-methylpyrazolo[1,5-a pyrimidine-3-carboxylate (J. Med. Chem. 1981, 24(5). 610-13) was heated in 1N aqueous sodium hydroxide solution until all has passed into solution. The reaction mixture was cooled and its pH was adjusted to 1 with aqueous hydrochloric acid. The resulting precipitate was filtered off, dried and recrystallized from dimethylformamide. There was obtained 7-mercapto-5-methyl-pyrazolo[1,5-a]pyrimidine-3-carboxylic acid as a yellow powder having a of melting point of 161°-162° (dec.).

b) A suspension of 105 g of 7-mercapto-5-methylpyrazolo[1,5-a]pyrimidine-3-carboxylic acid in 400 ml of methylene chloride was treated with 6.3 ml of 1-chloro-N,N,2-trimethyl-1-propenamine and treated in an ultrasound bath until the majority has passed into solution. The mixture was suction filtered over a glass fiber filter, and ammonia was conducted into the clear filtrate at 20°. A crystalline precipitate formed which was filtered off under suction, dried and subsequently triturated in 100 ml of H₂O for 5 minutes. The insoluble material was filtered off and the filtrate was concentrated in a vacuum to half of the volume. Upon allowing to stand at 0°, there was obtained 7-mercapto-5-methylpyrazolo[1,5-a]pyrimidine-3-carboxamide as the ammonium salt in the form of white crystals.

¹H NMR (DMSO-d ): δ2.28 (s, 3H); 6.65 (s, 1H); 7.00 (broad s, 1H): 7.17 (broad s, 4H, NH+); 7.94 (broad s, 1H) ppm.

c) A mixture of 2.80 g of 7-mercapto-5-methylpyrazolo[1,5-a]pyrimidine-3-carboxamide ammonium salt and 3.38 g of (7R)-7-aminocephalosporanic acid was treated with 25 ml of a 20 percent solution of boron trifluoride in acetonitrile and stirred at 20° for 40 minutes. The reaction mixture was treated with 30 ml of water and the pH was adjusted to 3.5 by means 28 percent aqueous sodium hydroxide solution. The precipitate thus formed was filtered off under suction and was chromatographed on OPTI-UP (C₁₂) (ANTEC AG, CH-Bennwil) using water as the eluent. There was obtained (6R,7R)-7-amino-3-[[(3-carbamoyl-5-methylpyrazolo[1,5-a]-pyrimidin-7-yl)thio]methyl]-8-oxo-5-thia-1-azabicyclo-[4.2.0]oct-2-ene-2-carboxylic acid.

¹H NMR (DMSO-d₆): δ2.60 (s, 3H); 3.56 (d, J=17.5 Hz, 1H); 3.78 (d, J=17.5 Hz, 1H); 4.30 (d, J=12.5 Hz, 1H); 4.43 (d, J=12.5 Hz). 1H): 4.82 (d, J=5 Hz, 1H): 5.04 (d, J=5 Hz. 1H); 7.20 (s, 1H); 7.50 (broad s, 1H); 7.56 (broad s, 1H); 8.48 (s. 1H) ppm.

IR (KBr) 1795.

d) A suspension of 2.05 g of (6R,7R)-7-amino-3-[[(3-carbamoyl-5-methylpyrazolo[1,5-a]pyrimidin-7-yl)thio]methyl]-8-oxo-5-thia-1-azabicyclo[4.2.0]oct-2-ene-2-carboxylic acid in 15 ml of acetonitrile and 15 ml of water was treated with 0.69 ml of triethylamine, whereupon a clear solution resulted. 2.28 g of 2-amino-4-thiazolethioglyoxylic acid s-(2-benzothiazolyl) ester were added to this solution. After stirring at 20° for 3 hours, the reaction mixture was suction filtered and the filtrate was partitioned between ethyl acetate and water. The aqueous phase was concentrated in a vacuum and the pH was adjusted to 2.3 with 3N hydrochloric acid, whereupon a yellow precipitate formed. After filtration, washing with water and drying, there was obtained (6R,7R)-7-(2-amino-4-thiazolglyoxylamido)-3-[[(3-carbamoyl-5-methylpyrazolo[1,5-a]pyrimidin-7-yl)thio]methyl]-8-oxo-5-thia-1-azabicyclo[4.2.0]oct-2-ene-2-carboxylic acid.

¹H NMR (DMSO-d₆): 2.61 (s, 3H): 3.62 (d, J=17.5 Hz, 1H); 3.82 (d, J=17.5 Hz, 1H); 4.36 (d, J=12.5 Hz, 1H); 4.47 (d, J=12.5 Hz, 1H); 5.22 (d, J ᴛᴍ 5 Hz, 1H); 5.78 (dd, J=8 and 5 Hz, 1H); 7.22 (s, 1H); 7.49 (broad s, 1H); 7.56 (broad s, 2H); 7.84 (s, 1H); 8.48 (s, 1H); 9.82 (d, J=8 Hz, 1H) ppm.

IR (KBr) 1779.

EXAMPLE 9

(6R,7R)-7-(2-Amino-4-thiazoleglyoxylamido)-3-[[(3-carbamoyl-7-(trifluoromethyl)pyrazolo[1,5-a]pyrimidin-5-yl)thio]methyl]-8-oxo-5-thia-1-azabicyclo[4.2.0]oct-2-ene-2-carboxylic acid was reacted with 4-[[(aminoxy)methyl]sulphonyl]pyrocatechol according to the procedure described in Example 7. After purification of the product with the chromatographic procedure in Example 7 and lyophilization of the product, there was obtained (6R,7R)-7-[(Z)-2-(2-amino-4-thiazolyl)-2-[[[(3,4-dihydroxyphenyl)-sulphonyl]methoxy]imino]acetamido]-3[[(3-carbamoyl-7-(tri-fluoromethyl)pyrazolo[1,5a]pyrimidin-5-yl)thio]methyl]-8-oxo-5-thia-1-azabicyclo[4.2.0]oct-2-ene-2-carboxylic acid as a pale yellow powder.

$^1$H NMR (DMSO-d$_6$): δ3.56 (d. J=18 Hz, 1H); 3.73 (d, 18 Hz, 1H); 4.27 (d, J=14 Hz, 1H); 4.60 (d, J=14 Hz, 1H); 5.12 (d, J=5 Hz, 1H); 5.14 (d, J=13 Hz, 1H); 5.23 (d, J=13 Hz, 1H); 5.74 (dd, J=8 and 5 Hz, 1H); 6.67 (s, 1H); 6.90 (d, 8 Hz, 1H); 7.1–7.6 (m, about 6H); 7.82 (s, 1H); 8.58 (s, 1H); 9.68 (s, 1H); 9.71 (d, J=8 Hz, 1H); 10.09 (s, 1H) ppm.

The (6R,7R)-7-(2-amino-4-thiazoleglyoxylamido)-3-[[(3-carbamoyl-7-(trifluoromethyl)pyrazolo[1,5-a]pyrimidin-5-yl)thio]methyl]-8-oxo-5-thia-1-azabicyclo[4.2.0]-oct-2-ene-2-carboxylic acid used as the starting compound above was prepared as follows:

a) A mixture of 11.5 g of methyl 5-aminopyrazole-4-carboxylate, 16 ml of ethyl ω, ω, ω-trifluoroacetoacetate and 150 g of polyphosphoric acid was heated to 100° while stirring for 16 hours. After cooling to 20°, cold water was added and the mixture was extracted with ethyl acetate. The organic phase was washed with 1N aqueous hydrochloric acid and aqueous saturated sodium chloride solution and then dried over Na$_2$SO$_4$. The solvent was evaporated in a vacuum and the residue was taken up in ether. The solid product was filtered off under suction and recrystallized from 2-propanol. There was obtained an isomer of the product, namely methyl 7-hydroxy-5-(trifluoromethyl)pyrazolo[1,5-a]pyrimidine-3-carboxylate of m.p. 216°–217°. The product enriched in the mother liquors was crystallized from ethyl acetate. There was obtained methyl 5-hydroxy-7-(trifluoromethyl)pyrazolo[1,5-a]pyrimidine-3-carboxylate of m.p. 149°–150°.

b) A mixture of 2.70 g of methyl 5-hydroxy-7-(trifluoromethyl)pyrazolo[1,5-a]pyrimidine-3-carboxylate and 1.26 g of 4-dimethylaminopyridine was heated to 100° for 2.5 hours in 50 ml of phosphorus oxychloride. The resulting solution was concentrated in a vacuum and then partitioned between ethyl acetate and saturated sodium chloride solution. The organic phase was washed in succession with 1N hydrochloric acid and saturated sodium chloride solution, dried over sodium sulphate, freed from solvent in a vacuum and the residue was crystallized from ethyl acetate/petroleum ether. There was obtained methyl 5-chloro-7-(trifluoromethyl)pyrazolo[1,5-a]pyrimidine-3-carboxylate as white crystals of m.p. 126°–127°.

c) A mixture of 2.30 g of methyl 5-chloro-7-(trifluoromethyl)pyrazolo[1,5-a]pyrimidine-3-carboxylate and 2.0 g of sodium hydrogen sulphide monohydrate in 60 ml of water was stirred at 60° for 1 hour. The reaction mixture was cooled, acidified with hydrochloric acid and extracted with ethyl acetate. The organic phase was washed with saturated sodium chloride solution, dried over sodium sulphate and concentrated in a vacuum until crystallization occurred. Petroleum ether was added and the solid product was filtered off under suction. There was obtained methyl 5-mercapto-7-(trifluoromethyl)pyrazolo[1,5-a]pyrimidine-3-carboxylate.

$^1$H NMR (DMSO-d$_6$): δ3.82 (s, 3H); 7.30 (s, 1H); 8.40 (s, 1H) ppm.

d) A solution of 1.80 g of methyl 5-mercapto-7-(trifluoromethyl)pyrazolo[1,5-a]pyrimidine-3-carboxylate in 800 ml of 25 percent aqueous ammonia was allowed to stand at 20° for 24 hours. The solution was concentrated to a small volume in a vacuum, made acidic with 1N hydrochloric acid and extracted with ethyl acetate. The organic phase was washed with saturated sodium chloride solution, dried over sodium sulphate and evaporated in a vacuum. The residual crystal slurry was treated with petroleum ether and filtered. There was obtained 5-mercapto-7-(trifluoromethyl)pyrazolo[1,5-a]pyrimidine-3-carboxamide.

$^1$NMR (DMSO-d$_6$): δ7.28 (s, 1H); 7.62 (broad s, 1H); 8.08 (broad s, 1H); 8.45 (s, 1H) ppm.

e) A mixture of 1.60 g of 5-mercapto-7-(trifluoromethyl)pyrazolo[1,5-a]pyrimidine-3-carboxamide and 1.66 g of (7R)-7-aminocephalosporanic acid in 120 ml of acetonitrile was treated while stirring with 20 ml of a 20 percent solution of boron trifluoride in acetonitrile and stirred at 20° for a further 5 hours. 100 ml of water were added and the mixture was concentrated in a vacuum to a volume of about 80 ml. The pH was adjusted to 2.8 with 25 percent aqueous ammonia. After stirring for 1 hour, the precipitate obtained was filtered, washed in succession with water acetone and ether and dried. There was obtained (6R,7R)-7-amino-3-[[(3-carbamoyl-7-(trifluoromethyl)pyrazolo[1,5-a]-pyrimidin-5-yl)thio]methyl]-8-oxo-5-thia-1-azabicyclo-[4.2.0]oct-2-ene-2-carboxylic acid.

$^1$H NMR (DMSO-d$_6$): δ3.53 (d, J=17.5 Hz, 1H); 3.72 (d, J=17.5 Hz, 1H); 4.24 (d, J=12.5 Hz, 1H); 4.58 (d, J=12.5 Hz, 1H); 4.80 (d, J=5 Hz, 1H); 4.98 (d, J=5 Hz, 1H); 7.35 (broad s, 1H); 7.52 (broad s, 1H); 7.82 (s, 1H); 8.57 (s, 1H) ppm.

f) A suspension of 1.425 g of (6R,7R)-7-amino-3-[[(3-carbamoyl-7-(trifluoromethyl)pyrazolo[1,5-a]pyrimidin-5-yl)thio]methyl]-8-oxo-5-thia-1-azabicyclo[4.2.0]oct-2-ene-2-carboxylic acid was treated with 0.475 ml of N,O-bis(trimethylsilyl)acetamide. After a clear solution had been obtained, 1.20 g of 2-amino-4-thiazolethioglyoxylic acid s-(2-benzothiazolyl) ester were added and the mixture was stirred at 20° for 2.5 hours. The reaction mixture was filtered through a glass fiber filter, the filtrate was concentrated in a vacuum and partitioned between ethyl acetate and 0.25M potassium hydrogen carbonate solution. The aqueous phase was concentrated in a vacuum and then chromatographed on Opti-Up (C$_{12}$), with elution being carried out first with water and then with water/acetonitrile mixtures using increasing amounts of acetonitrile. The product fractions were combined, concentrated in a vacuum and adjusted to pH 2 with 3N hydrochloric acid, upon which a precipitate formed. There was obtained (6R,7R)-7-(2amino-4-thiazoleglyoxylamido)-3-[[(3-carbamoyl-7-(tri-fluoromethyl)pyrazolo[1,5-a]pyrimidin-5-yl)thio]methyl]-8-oxo-5-thia-1-azabicyclo[4.2.0]oct-2-ene-2-carboxylic acid.

$^1$H NMR (DMSO-d$_6$): δ3.60 (d, J=18 Hz, 1H); 3.77 (d, J=18 Hz, 1H); 4.30 (d, J=12 Hz, 1H); 4.62 (d, J=12 Hz, 1H); 5.20 (d, J=5 Hz, 1H); 5.76 (dd, J=8 Hz and J=5 Hz, 1H); 7.33 (s, 1H); 7.40 (s, 2H); 7.50 (s, 1H); 7.80

(s, 1H); 7.83 (s, 1H); 8.57 (s, 1H); 9.29 (d, J=8 Hz, 1H) ppm.
IR (KBr): 1775
MS: 629 (M+H)+.

EXAMPLE 10

34 mg of (6R,7R)-7-(2-amino-4-thiazoleglyoxylamido)-3-[[(2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid were reacted with 28 mg of 2-[2-(aminooxy)-2-methylpropionyl]-1-[(3,4-dihydroxyphenyl)sulphonyl]hydrazine according to the procedure described in Example 7. After purification of the crude product with the chromatographic procedure described in Example 1 and lyophilization of the product, there was obtained (6R,7R)-7-[(Z)-2-(2-amino-4-thiazolyl)-2-[[1-[3-[(3,4-dihydroxy-phenyl)sulphonyl]carbazolyl]-1-methylethoxy]imino]aceta-mido]-3-[[(2-carbamoyl)-5-methyl-s-triazolo[1,5-a]-pyrimidin-7-yl)-thio]methyl]-8-oxo-5-thia-1-azabicyclo-[4.2.0]oct-2-ene-2-carboxylic acid as a white powder.

$^1$H NMR (DMSO-d$_6$): δ1.25 (s, 3H); 1.27 (s, 3H); 2.60 (s, 3H); 3.66 (d, J=18 Hz, 1H); 3.86 (d, J=18 Hz, 1H); 4.42 (d, J=13 Hz, 1H); 4.56 (d, J=13 Hz, 1H) 5.24 (d, J=5 Hz, 1H); 5.86 (dd, J=8 and 5 Hz, 1H); 6.79 (d, J=9 Hz, 1H); 6.82 (s, 1H); 7.09 (dd, J=9 and 1.5 Hz, 1H); 7.19 (d, J=1.5 Hz, 1H); 7.31 (broad s, 1H); 7.41 (broad s, 1H); 7.86 (s, 1H); 8.23 (s, 1H); 9.37 (d, J=4 Hz, 1H); 9.45 (d, J=4 Hz, 1H); 9.6-10.00 (m, about 3H) ppm.

The 2-[2-(aminooxy)-2-methylpropionyl]-1-[(3,4-dihydroxyphenyl)sulphonyl]hydrazine used as the starting material was prepared as follows:

a) 2.9 g of 3,4-diacetoxy-benzenesulphochloride were added to a mixture of 5.15 g of hydrazine hydrate and 10 ml of water and the mixture was heated to 70° C. for 1 hour. The clear solution was cooled and the solvent is evaporated off in a vacuum. The residue was taken up in water and chromatographed on MCI gel CHP2OP. Elution was carried out first with water and subsequently with water/methanol mixtures using increasing amounts of methanol. The product fractions were concentrated completely in a vacuum and the residue was crystallized from methanol/diethyl ether. There was obtained 3,4-dihydroxybenzenesulphonic hydrazide as white crystals having a melting point of 172° C. (dec.).

b) A mixture of 204 mg of 3 4-dihydroxybenzenesulphonic hydrazide and 379 mg of 2-methyl-2-(phthalimidooxy)thiopropionic acid S-(2-benzothiazolyl) ester was heated to 60° C. in 5 ml of acetonitrile for 3 hours. After cooling, any undissolved material was filtered off under suction. The filtrate was freed from solvent in a vacuum and the residue was taken up in 3 ml of ethanol. The suspension was treated with 100 mg of hydrazine hydrate and stirred at 20° C. for 1 hour. A clear solution first resulted, from which a white precipitate separated out. Undissolved material was filtered off and the filtrate was evaporated in a vacuum. The crystalline residue was triturated with 10 ml of 0.1N aqueous hydrochloric acid for 10 minutes and the insoluble material was separated by filtration. The filtrate was adjusted to pH 7 by the addition of 2N aqueous sodium hydroxide solution and chromatographed on MCI gel CHP2OP, with elution being carried out first with 2% aqueous acetic acid and then with water/methanol (9:1, v/v). By evaporation of the product fractions in a vacuum there was obtained 2-[2-(aminooxy)-2-methylpropionyl]-1-[(3,4-di-hydroxyphenyl)sulphonyl]hydrazine as white crystals of melting point 220° C. (dec.).

$^1$H NMR (DMSO-d$_6$): δ1.10 (s, 6H); 5.89 (broad s, 2H); 6.78 (d, J=8 Hz, 1H); 7.09 (dd, J=8 and 2 Hz, 1H); 7.16 (d, J=2 Hz, 1H) ppm.

EXAMPLE 11

122 mg of 4-[[(aminooxy)methyl]sulphonyl]pyrocatechol were reacted with 236 mg of (6R,7R)-7-(2-amino-4-thiazoleglyoxylamido)-3-[[[2-(methoxycarbonyl)-5-methyl-s-triazolo[1,5-a]pyrimidin-7-yl]thio]methyl]-8-oxo-5-thia-1-azabicyclo[4.2.0]oct-2-ene-2-carboxylic acid according to the procedure described in Example 7. The crude product obtained was suspended in 10 ml of water and brought into solution by the slow addition of 0.1N sodium hydroxide solution, with care being taken that the pH of the solution did not exceed 7. By chromatography on MCI gel CHP 2OP using water as the elution agent as well as water/methanol mixtures with increasing amounts of methanol and lyophilization of the concentrated product fractions, there was obtained (6R,7R)-7-[(Z)-2-(2-amino-4-thiazolyl)-2-[[[(3,4-dihydroxyphenyl)sulphonyl]methoxy]imino]acetamido]-3-[[(2-(methoxycarbonyl)-5-methyl-s-triazolo[1,5-a]pyrimidin-7-yl)thio]methyl]-8-oxo-5-thia-1azabicyclo[4.2.0]oct-2-ene-2-carboxylic acid monosodium salt as a white powder.

$^1$H NMR (DMSO-d$_6$) δ2.61 (s, 3H); 3.11 (d, J=18 Hz, 1H); 3.47 (d, J=18 Hz, 1H); 3.93 (s, 3H); 4.35 (d, J=15 Hz, 1H); 4.56 (d, J=15 Hz, 1H); 4.91 (d, J=5 Hz, 1H); 5.11 (d, J=15 Hz, 1H); 5.20 (d, J=15 Hz, 1H); 5.42 (dd, J=7 Hz and 5 Hz, 1H); 6.78 (s, 1H); 6.86 (d, J=8 Hz, 1H); 7.16 (d, J=1 Hz, 1H); 7.22-7.36 (m, about 4H); 7.84 (s, 1H); 9.43 (d, J=7 Hz, 1H) ppm.

The starting material was prepared as follows:

a) 1.10 g of methyl 7-mercapto-5-methyl-s-triazolo[1,5-a]pyrimidine-2-carboxylate and 1.34 g of (7R)-7-amino-cephalosporanic acid were suspended in 5 ml of acetonitrile and treated with 10 ml of a 20 percent solution of boron trifluoride in acetonitrile and stirred at 20° for 90 minutes. The reaction mixture was treated with 40 ml of water and the pH was adjusted to 2.5 by means of 28 percent sodium hydroxide solution. After stirring at 0° for 1 hour, the precipitate was filtered off under suction and dried. There was obtained (6R,7R)-7-amino-3-[[2-(methoxycarbonyl)-[5-methyl-s-triazolo[1,5-a]pyrimidin-7-yl]thio]methyl]-8-oxo-5-thia-1-azabicyclo[4.2.0]oct-2-ene-carboxylic acid as a white powder.

$^1$H NMR (DMSO-d$_6$) δ2.62 (s, 1H); 3.57 (d, J=18 Hz, 1H); 3.77 (d, J=18 Hz, 1H); 3.94 (s, 3H); 4.37 (d, J=12 Hz, 1H); 4.45 (d, J=12 Hz, 1H); 4.86 (d, J=5 Hz, 1H); 5.04 (d, J=5 Hz, 1H); 7.44 (s, 1H) ppm.
IR (KBr): 1784 cm$^{-1}$.

b) 1.50 g of (6R,7R)-7-amino-3-[[2-(methoxycarbonyl)-[5-methyl-s-triazolo[1,5-a]pyrimidin-7-yl)thio)-methyl]-8-oxo-5-thia-1-azabicyclo[4.2.0]oct-2-ene-carboxylic acid in 7.5 ml of acetonitrile and 7.5 ml of water were brought into solution with 0.49 ml of triethylamine. The solution was treated with 1.50 g of 2-amino-4-thiazolethioglyoxylic acid S-(2-benzothiazolyl) ester and stirred at 20° for 1hour. The reaction mixture was partitioned between water and ethyl acetate and the aqueous phase was chromatographed on Optiup (C$_{12}$) (Antec AG, CH-Bennwil) with a gradient of 0% to 10% acetonitrile in water. The product fractions were concentrated to about 25 ml and the pH was adjusted to 2.5. The precipitate was filtered off under suction and dried. There was obtained (6R,7R)-7-(2-amino-4-thiazole-glyoxylamido)-3-[[[2-(methoxycarbonyl)-5- methyl-s-triazolo-[1,5-a]pyrimidin-7-yl) thio]methyl]-8-oxo-5-thia-1-aza-bicyclo[4.2.0]oct-2-ene-2carboxylic acid as a yellow powder.

$^1$H NMR (DMSO-d$_6$) δ2.62 (s, 3H), 3.62 (d, J=18 Hz, 1H); 3.80 (d, J=18 Hz, 1H); 3.94 (s, 3H); 4.40 (d, J=12 Hz, 1H); 4.50 (d, J=12 Hz, 1H); 5.20 (d, J=5 Hz, 1H); 5.78 (dd, J=8 Hz and J=5 Hz, 1H); 7.41 (s, 2H); 7.46 (s, 1H); 7.82 (s, 1H); 9.81 (d, J=8 Hz, 1H) ppm.

IR (KBr): 1776 cm$^{-1}$.

EXAMPLE 12

307 mg of 4-[[(aminooxy)methyl]sulphonyl]pyrocatechol were reacted with 531 mg of (6R,7R)-7-(2-amino-4-thiazoleglyoxylamido)-3-[[(7-methylpyrazolo[1,5-a]pyrimidin-5-yl)thio]methyl]-8-oxo-5-thia-1-azabicyclo[4.2.0]oct-2-ene-2-carboxylic acid in an analogous manner to the procedure described in Example 11 or Example 7. There was obtained (6R,7R)-7-[(Z)-2-(2-amino-4-thiazolyl)-2-[[[(3,4-dihydroxyphenyl)sulphonyl]methoxy]imino]acetamido]-3-[[(7-methylpyrazolo[1,5-a]pyridin-5-yl)thio]methyl-8-oxo-5-thia-1-azabicyclo[4.2.0]oct-2-ene-2-carboxylic acid monosodium salt as a white powder.

$^1$H NMR (DMSO-d$_6$): δ2.63 (s,3H); 3.11 (d, J=18 Hz, 1H); 3.49 (d, J TM 18 Hz, 1H); 4.21 (d, J=13 Hz, 1H); 4.49 (d, J=13 Hz, 1H); 4.94 (d, J=5 Hz, 1H); 5.20 (d, J=14 Hz, 1H); 5.27 (d, J=14 Hz, 1H); 5.46 (m, 1H); 6.54 (d, J=1 Hz, 1h) 6.76 (s, 1H); 6.79 (d, J=10 Hz, 1H); 6.93 (s, 1H); 7.10 (d, J=1 Hz, 1H); 7.19 (dd, J=10 and 1 Hz, 1H); 8.09 (d, J=1 Hz, 1H); 9.44 (broad s, 1H) ppm.

The starting material was be prepared as follows:

a) 7.20 g of methyl 5-mercapto-7-methylpyrazolo[1,5-a]-pyrimidine-3-carboxylate were heated to 100° in 2N sodium hydroxide solution until almost all had dissolved. The solution was cooled, filtered and the filtrate was adjusted to pH 2. The product was filtered off under suction, washed with water and acetone and dried. There was obtained 5-mercapto-7-methylpyrazolo[1,5-a]pyrimidine-3-carboxylic acid of m.p. 225° (dec.).

$^1$H NMR (DMSO-d$_6$) δ2.50 (s, 3H); 6.80 (s, 1H); 8.25 (s, 1H) ppm.

MS (70 eV): 209 (M+).

b) 2.00 g of 5-mercapto-7-methylpyrazolo[1.5-a]pyrimidine-3-carboxylic acid were heated to 220° under argon for 1 hour. After cooling, the reaction mixture was taken up in 10 percent potassium hydrogen carbonate solution. The insoluble portion was filtered off under suction and taken up in water. The solution was acidified to pH 2 and the precipitate was filtered off under suction. After drying, there was obtained 7-methylpyrazolo[1,5-a]pyrimidine-5-thiol.

$^1$H NMR (DMSO-d$_6$); δ2.50 (s, 3H); 6.04 (d, J=2 Hz, 1H); 6.71 (s, 1H); 7.93 (d, J=2 Hz, 1H); 13.8 (s, broad, 1H) ppm.

MS (70 eV): 165 (M+).

c) 0.70 g of 7-methylpyrazolo[1,5-a]pyrimidine-5-thiol and 1.15 g of (7R)-7-amino-cephalosporanic acid were dissolved in 10 ml of a 20 percent solution of boron trifluoride in acetonitrile and stirred at room temperature for 1 hour. The reaction mixture was concentrated and taken up in 10 ml of water. The solid was filtered off under suction. There was obtained (6R,7R)-7-amino-3-[[(7-methylpyrazolo[1,5-a]pyrimidin-5-yl)thio]methyl]-8-oxo-5-thia-1-azabicyclo[4.2.0]oct-2-ene-2-carboxylic acid as a reddish powder.

$^1$H NMR (DMSO-d$_6$) δ2.64 (s, 3H); 3.48 (d, J=18 Hz, 1H); 3.74 (d, J=18 Hz, 1H); 3.97 (d, J=12 Hz, 1H); 4.72 (d, J=12 Hz, 1H); 4.78 (d, J=5 Hz, 1H); 4.98 (d, J=5 Hz, 1H); 6.56 (d, J TM 2 Hz, 1H); 6.88 (s, 1H); 8.12 (d, J=2 Hz, 1H) ppm.

IR (KBr): 1799 (cm−).

d) 1.00 g of (6R,7R)-7-amino-3-[[(7-methylpyrazolo[1,5-a]pyrimidin -5-yl]thio]methyl]-8-oxo-5-thia-1-azabicyclo[4.2.0]oct-2-ene-2-carboxylic acid was brought into solution in 5 ml of acetonitrile and 5 ml of water with 0.37 ml of triethylamine. The solution was treated with 1.0 g of 2-amino-4-thiazolethioglyoxylic acid S-(2-benzothiazolyl) ester and stirred at 20° for 1 hour. The reaction mixture was partitioned between water and ethyl acetate and the aqueous phase was chromatographed on Optiup (C$_{12}$) (Antec AG, CH-Bennwil) with a gradient of 0% to 10% acetonitrile in water. The product fractions Were concentrated to 10 ml and adjusted to pH 2.2 with HCl. The precipitate was filtered off under suction. There was obtained (6R,7R)-7-(2-amino-4-thiazoleglyoxylamido)-3-[[7-methylpyrazolo[1,5-a]pyrimidin-5-yl)thio]methyl]-8-oxo-5-thia-1-azabicyclo[4.2.0]oct-2-ene-2-carboxylic acid as a yellow powder.

$^1$H NMR (DMSO-d$_6$): δ2.64 (s, 3H); 3.54 (d, J=18 Hz, 1H); 3.28 (d, J=18 Hz, 1H); 4.00 (d, J=12 Hz, 1H); 4.78 (d, J=12 Hz, 1H); 5.14 (d, J=5 Hz, 1H); 5.72 (dd, J=8 Hz and J=5 Hz, 1H); 6.56 (d, J=2 Hz, 1H); 6.89 (s, 1H); 7.43 (s, 2H); 7.80 (s, 1H); 8.12 (s, 1H); 9.79 (d, J=8 Hz, 1H) ppm.

IR (KBr): 1776 (cm$^{-1}$.

EXAMPLE 13

307 mg of 4-[[(aminooxy)methyl]sulphonyl]pyrocatechol were reacted with 575 mg of (6R,7R)-7-(2-amino-4-thiazoleglyoxylamido)-3-[[(3-carboxy-7-methylpyrazolo[1,5-a]pyrimidin-5-yl)thio]methyl]-8-oxo-5-thia-1-azabicyclo[4.2.0]oct-2-ene-2-carboxylic acid in an analogous manner to the procedure described in Examples 11 or 7. There was obtained (6R,7R)-7-[(Z)--2-(2-amino-4-thiazolyl)-2-[[[(3,4-dihydroxyphenyl)sulphonyl]methoxy]imino]acetamido]-3-[[(3-carboxy-7-methylpyrazolo[1,5-a]pyrimidin-5-yl)thio]methyl]-8-oxo-5-thia-1-azabicyclo[4.2.0]oct-2-ene-2-carboxylic acid as a white powder.

$^1$H NMR (DMSO-d$_6$) δ2.67 (s, 3H); 3.68 (d, J=18 Hz, 1H); 3.81 (d, J=18 Hz, 1H) 4.20 (d, J=14 Hz, 1H); 4.55 (d, J=14 Hz, 1H); 5.12 (d, J=5 Hz, 1H); 5.15 (d, J=13 Hz, 1H); 5.23 (d, J=13 Hz, 1H); 5.70 (dd, J=8 and 5 Hz, 1H); 6.67 (s, 1H); 6.90 (d, J=9 Hz,1H); 7.09–7.23 (m, 3H); 7.28 (broad s, 2H); 8.48 (s, 1H); 9.69 (d, J=8 Hz, 1H); 10.10 (broad s, 1H) ppm.

The starting material was prepared as follows:

a) A suspension of 4.00 g of (7R)-7-aminocephalosporanic acid and 3.34 g of 5-mercapto-7-methylpyrazolo[1,5-a]pyrimidine-3-carboxylic acid in 20 ml of acetonitrile was treated with 25 ml of a 20 percent solution of boron trifluoride in acetonitrile and the mixture was stirred at 20° for 1.5 hours. 150 ml of cold water were added and the mixture was stirred at 0° for 1.5 hours. The precipitate was filtered off under suction and dried. There was obtained (6R,7R)-7-amino-3-[[(3-carboxy-7-methylpyrazolo[1,5-a]pyri-midin-5-yl)thio]methyl]-8-oxo-5-thia-1-azabicyclo[4.2.0]-oct-2-ene-2-carboxylic acid as an almost colorless powder.

$^1$H NMR (DMSO-d$_6$) δ2.67 (s, 3H); 3.76 (m, 2H); 4.18 (d, J=12 Hz, 1H); 4.52 (d, J=12 Hz, 1H); 4.80 (d, J=5

Hz, 1H); 5.00 (d, J=5 Hz, 1H); 7.14 (s, 1H); 8.47 (s, 1H) ppm. MS (70 eV) 422 (M+H)+.

b) 3.00 g of (6R,7R)-7-amino-3-[[(3-carboxy-7-methylpyrazolo[1.5-a]pyrimidine-5-yl)thio]methyl]-8-oxo-5-thia-1-azabicyclo[4.2.0]oct-2-ene-2-carboxylic acid were brought into solution in 15 ml of acetonitrile and 15 ml of water with 1.02 ml of triethylamine. The solution was treated with 3.15 g of 2-amino-4-thiazolethioglyoxylic acid S-(2-benzothiazolyl) ester and stirred for 1 hour. The reaction mixture was partitioned between water and ethyl acetate and the aqueous phase was chromatographed on Optiup ($C_{12}$) (Antec AG, CH-Bennwil) with a gradient of 0% to 20% acetonitrile in water. The product fractions were concentrated to about 50 ml and the pH was adjusted to 2.5. The precipitate was filtered off under suction. After drying, there was obtained (6R,7R)-7-(2-amino-4-thiazole-glyoxylamido)-3-[[(3-carboxy-7-methylpyrazolo[1,5a]pyrimidin-5-yl)thio]methyl]-8-oxo-5-thia-1-azabicyclo[4.2.0]oct-2-ene-2-carboxylic acid as a yellow powder.

$^1$H NMR (DMSO-$d_6$): δ2.67 (s, 3H); 3.83 (m, 2H); 4.22 (d, J=12 Hz, 1H); 4.54 (d, J=12 Hz, 1H); 5.17 (d, J=5 Hz, 1H); 5.71 (dd, J=8 Hz and J=5 Hz, 1H); 7.15 (s, 1H); 7.41 (s, 2H); 7.80 (s, 1H); 8.47 (s, 1H); 9.76 (d, J=8 Hz, 1H) ppm.

IR (KBr): 1778 cm$^{-1}$.

EXAMPLE 14

613 m9 of 4-[[(aminooxy)methyl]sulphonyl]pyrocatechol were reacted with 1.06 g of (6R,7R)-7-(2-amino-4-thiazoleglyoxylamido)-3-[[(5-methylpyrazolo]1,5-a]pyrimidin-7-yl)thio]methyl]-8-oxo-5-thia-1-azabicyclo[4.2.0]oct-2-ene-2-carboxylic acid in an analogous manner to the procedure described in Example 11 or Example 7. There was obtained (6R,7R)-7-[(Z)-2-(2-amino-4-thiazolyl)-2-[[[(3,4-dihydroxyphenyl)sulphonyl]methoxy]imino]acetamido]-3-[[(5-methylpyrazolo[1,5-a]pyrimidin-7-yl)thio]methyl-8-oxo-5-thia-1-azabicyclo[4.2.0]oct-2-ene-2-carboxylic acid monosodium salt as a white powder.

$^1$H NMR (DMSO-$d_6$) δ2.50 (s, 3H); 3.17 (d, J=18 Hz, 1H); 3.50 (d, J=18 Hz, 1H); 4.27 (d, J=14 Hz, 1H); 4.53 (d, J=14 Hz, 1H); 4.96 (d, J=5 Hz, 1H); 5.09 (d J=13 Hz, 1H); 5.15 (d, J=13 Hz, 1H); 5.46 (d, J=5 Hz, 1H); 6.51 (d, J=0.2 Hz, 1H); 6.72 (d, J=8 Hz, 1H); 6.77 (s, 1H); 7.06 (d, J=0.2 Hz, 1H); 7.17 (dd, J=8 and 0.2 Hz, 1H); 7.31 (s,. 1H); 8.11 (d, J=0.2 Hz, 1H); 9.48 (broad s, 1H) ppm.

The starting material was prepared as follows:

a) 110 g of 7-mercapto-5-methylpyrazolo[1,5-a]pyrimidine-3-carboxylic acid were heated to reflux temperature for 2.5 hours in 500 ml of 20 percent hydrochloric acid. The reaction mixture was cooled, the product was filtered off under suction and then recrystallized from water/ethanol at a pH of 6. There was obtained 5-methylpyrazolo [1,5-a]pyrimidine-7-thiol as yellow crystals of a melting point above 250°.

$^1$H NMR (DMSO-$d_6$): δ2.33 (s, 3H); 6.31 (d, J=2 Hz, 1H); 6.67 (s, 1H); 8.06 (d, J=2 Hz, 1H) 13.3 (s, broad, 1H) ppm.

MS (70 eV): 165 (M+).

b) 1.1 g of 5-methylpyrazolo[1,5-a]pyrimidine-7-thiol and 1.80 g of (7R)-7-aminocephalosporanic acid were stirred for 1 hour in 18 ml of a 20 percent solution of boron trifluoride in acetonitrile. The reaction mixture was concentrated, the residue was taken up in 15 ml of water, and the pH was adjusted to 2.5 with 2N sodium hydroxide solution. The precipitated product was filtered off under suction and dried. There was obtained (6R,7R)-7-amino-3-[[(5-methylpyrazolo[1,5-a]pyrimidin-7-yl)thio]methyl]-8-oxo-5-thia-1-azabicyclo4.2.0]oct-2-ene-2-carboxylic acid.

$^1$H NMR (DMSO-$d_6$) δ2.50 (s, 1H); 3.54 (d, J=18 Hz, 1H); 3.77 (d, J=18 Hz, 1H); 4.24 (d, J=12 Hz, 1H); 4.40 (d, J=12 Hz, 1H); 4.80 (d, J=5 Hz, 1H); 5.03 (d, J=5 Hz,, 1H); 6.57 (d, J=2 Hz, 1H); 6.98 (s, 1H); 8.15 (d, J=2 Hz, 1H) ppm.

IR (KBr): 1794.

c) 2.30 g of (6R,7R)-7-amino-3-[[(5-methylpyrazolo[1,5-a]pyrimidin-7-yl)thio]methyl]-8-oxo-5-thia-1-azabicyclo[4.2.0]oct-2-ene-2-carboxylic acid were brought into solution in 12.5 ml of water and 12.5 ml of acetonitrile with 0.80 ml of triethylamine. The solution was treated with 2.30 g of 2-amino-4-thiazolethioglyoxylic acid S-(2-benzothiazolyl) ester and stirred at 20° for 45 minutes. The reaction mixture was partitioned between water and ethyl acetate and the aqueous phase was chromatographed on Optiup ($C_{12}$) (Antec AG, Bennwil) with a gradient of 0% to 10% acetonitrile in water. The product fractions were concentrated and the pH was adjusted to 2.2. The precipitate was filtered off under suction and dried. There was obtained (6R,7R)-7-(2-amino-4-thiazoleglyoxylamido)-3-[[(5-methylpyrazolo [1,5-a]pyrimidin-7-yl)thio]methyl]-8-oxo-5-thia-1-azabicyclo[4.2.0]oct-2-ene-2-carboxylic acid.

$^1$H NMR (DMSO-$d_6$): δ2.50 (s, 3H); 3.62 (d, J=18 Hz, 1H); 3.81 (d, J=18 Hz, 1H); 4.31 (d, J=12 Hz, 1H); 4.45 (d, J=12 Hz, 1H); 5.22 (d, J=5 Hz, 1H); 5.78 (dd, J=8 Hz and J=5 Hz, 1H); 5.67 (d, J=2 Hz, 1H); 6.99 (s, 1H); 7.42 (s, 2H); 7.82 (s, 1H); 8.16 (d, J=2 Hz, 1H); 9.84 (d, J=8 Hz, 1H) ppm.

IR (KBr): 1776 cm$^{-1}$.

EXAMPLE 15

120 mg of 4-[[(aminooxy)methyl]sulphonyl]pyrocatechol were reacted with 220 mg of (6R,7R)-7-(2-amino-4-thiazoleglyoxylamido)-3-[[2-(hydroxymethyl)-5-methyl-s-triazolo[1,5-a]pyrimidin-7-yl]thio]methyl]-8-oxo-5-thia-1-azabicyclo[4.2.0]oct-2-ene-2-carboxylic acid in an analogous manner to the procedure described in Example 11 or Example 7. The crude product was suspended in about 4 ml of water and brought into solution by the slow addition of 1N sodium hydroxide solution, with care being taken that the pH of the solution did not exceed 7. By chromatography on MCI gel CHP 2OP using 0.005M sodium phosphate buffer and increasing amounts of acetonitrile as the eluent, there was obtained purified product which was isolated by concentration and acidification of the pure fractions with 1N HCl. By dissolving this material in water with the addition of 1 equivalent of sodium hydroxide solution and subsequent lyophilization, there was obtained (6R,7R)-7-[(Z)-2-(2-amino-4-thiazolyl)-2-[[[(3,4-dihydroxyphenyl)sulphonyl]methoxy]imino]acetamido]-3-[[[2-(hydroxymethyl)-5-methyl-5-thiazolo[1,5-a]pyrimidin-7-yl]-thio]methyl]-8-oxo-5-thia-1-azabicyclo[4.2.0]oct-2-ene-2-carboxylic acid monosodium salt as a white powder.

$^1$H NMR (DMSO-$d_6$) δ inter alia 2.56 (s, 3H), 3.09 (d,J=18 Hz, 1H); 3.48 (d,J=18 Hz, 1H); 4.29 (d,J=14 Hz, 1H); 4.55 (d,J=14 Hz, 1H); 4.61 (s, 2H); 4.92 (d,J=5 Hz, 1H); 5.14 (d,J=13 Hz, 1H); 5.22 (d=13 Hz, 1H); 5.44 (m, 1H); 6.78 (s, 1H); 6.66 (d,J=8 Hz, 1H); 7.1-7.4 (m, 4H); 7.60 (s, 1H); 9.42 (d,J=8 Hz, 1H) ppm.

The starting material was prepared as follows:

a) 2.24 g of methyl 7-mercapto-5-methyl-s-triazolo[1,5-a]-pyrimidine-2-carboxylate were suspended in 350 ml of tetrahydrofuran and treated at 2° within 15 minutes with 40 ml of a 1M diisobutylaluminium hydride/hexane solution. The reaction mixture was stirred at 2° for 10 minutes and subsequently treated with ice. The reaction mixture was concentrated extensively, the residue was taken up in 30 ml of water, and the solution was acidified to pH 1.2 with concentrated hydrochloric acid. The solid was collected by filtration and dried in a high vacuum. There was obtained 7-mercapto-5-methyl-s-triazolo[1,5-a]pyrimidine-2-methanol of melting point 233° (dec.).

$^1$H NMR (DMSO-$d_6$) δ2.33 (s, 3H); 4.59 (s, 2H); 6.87 (s, 1H) ppm.

b) 0.400 q of 7-mercapto-5-methyl-s-triazolo[1.5-a]pyrimidine-2-methanol and 0.520 q of (7R)-7-aminocephalosporanic acid were dissolved in 5.0 ml of a 20 percent solution of boron trifluoride in acetonitrile and the solution was stirred at 20° for 30 minutes. The reaction mixture was diluted with 10 ml of water and adjusted to pH 3.0 with 2N sodium hydroxide solution. The resulting precipitate was filtered off and dried. There was obtained (6R,7R)-7-amino-3-[[[(2-hydroxymethyl)-5-methyl-s-triazolo[1.5-a]-pyrimidin-7-yl]thio]methyl]-8-oxo-5-thia-1-azabicyclo-[4.2.0]oct-2-ene-2-carboxylic acid as a beige powder.

$^1$H NMR (DMSO-$d_6$) δ2.57 (s, 3H); 3.54 (d,J=18 Hz, 1H); 3.75 (d,J=18 Hz, 1H); 4.31 (d,J=12 Hz, 1H); 4.44 (d,J=12 Hz, 1H); 4.62 (s, 2H); 4.81 (d,J=5 Hz, 1H); 5.02 (d,J=5 Hz, 1H); 7.25 (s, 1H).

c) 0.70 g of(6R,7R)-7-amino-3-[[[(2-hydroxy-methyl)-5-methyl-s-triazolo[1,5-a]pyrimidin-7-yl]thio]methyl]-8-oxo-5-thia-1-azabicyclo[4.2.0]oct-2-ene-2-carboxylic acid were suspended in 10 ml of N,N-dimethylformamide and 10 ml of methylene chloride and brought into solution by the addition of 1.62 ml of N,O-bis-(trimelhylsilyl)acetamide. The mixture was cooled to 0°, treated with 0.95 g of 2-amino-4-thiazolethio-glyoxylic acid S-(2-benzothiazolyl) ester and stirred at this temperature for 1.5 hours. The reaction mixture was partitioned between ethyl acetate and saturated sodium hydrogen carbonate solution. The aqueous phase was chromatographed on Opti-Up $C_{12}$ with water to 5% acetonitrile in water. Uniform fractions were concentrated and adjusted to pH 2.5 with 1N hydrochloric acid. The precipitated product was filtered off and dried in a high vacuum. There was obtained (6R,7R)-7-(2-amino-4-thiazoleglyoxylamido)-3-[[2-(hydroxymethyl)-5-methyl-s-triazolo-[1,5-a]pyrimidin-7-yl]thio]methyl]-8-oxo-5-thia-1-aza-bicyclo[4.2.0]oct-2-ene-2-carboxylic acid as a yellow powder.

$^1$H NMR (DMSO-$d_6$) δ2.58 (s, 3H); 3.60 (6,J=18 Hz, 1H); 3.82 (d,J=18 Hz, 1H); 4.37 (6,J=12 Hz, 1H); 4.50 (d,J=12 Hz, 1H); 4.62 (s, 2H); 5.22 (d,J=5 Hz, 1H); 5.77 (dd,J=5 and 8 Hz, 1H); 7.26 (s, 1H); 7.44 (s, broad 2H); 7.84 (s, 1H); 9.83 (d,J=8 Hz, 1H) ppm.

EXAMPLE 16

161 mg of 2-amino-4-thiazoleglyoxylic acid (Z)-O-[2-[(3,4-dihydroxyphenyl)sulphonamido]ethyl] oxime were reacted with 206 mg of (6R,7R)-7-amino-3-[[2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid hydrochloride according to the procedure described in Example 1. The working-up procedure described in Example 1 yielded an aqueous phase, which was adjusted to pH 9 and applied to a MCI gel column (CHP2OP) conditioned with 1% aqueous acetic acid. Elution was carried out first with 1% aqueous acetic acid, then with water, and finally with water/acetonitrile mixtures using increasing amounts of acetonitrile. The product was eluted with a 4:1 (v/v) water/acetonitrile mixture. By lyophilization of the product fractions, which were concentrated in a vacuum, there was obtained (6R,7R)-7-[(Z)-2-(2-amino-4-thiazolyl)-2-[[2-[(3,4-dihydroxyphenyl)sulphonamido]ethoxy]imino]acetamido]-3-[[(2-carbamoyl-5-methyl-s-triazolo[1,5-a]-pyrimidin-7-yl)thio]methyl]-8-oxo-5-thia-1-azabicyclo[4.2.0]oct-2-ene-2-carboxylic acid as a white powder.

$^1$H NMR (DMSO-$d_6$): δ2.61 (s, 3H); 2.98 (dt, J=7 and 7 Hz, 1H); 3.53 (d, J=17 Hz, 1H); 3.78 (d, J=17 Hz, 1H); 3.98 (t, J=7 Hz, 1H); 4.37 (d, J=13 Hz, 1H); 4.50 (d, J=13 Hz, 1H); 5.18 (d, J=5 Hz, 1H); 5.81 (dd, J=8 and 5 Hz, 1H); 6.74 (s, 1H); 6.86 (d, J=8 Hz, 1H); 7.09 (dd, J=8 and 2 Hz, 1H); 7.15 (d, J=2 Hz, 1H); 7.28 (broad s, 2H); 7.34 (t, J=7 Hz, 1H); 7.39 (s, 1H); 7.88 (s, 1H); 8.17 (s, 1H); 9.56 (d, J=8 Hz, 1H); 9.67 (broad s, 1H); 9.91 (broad s, 1H) ppm.

The 2-amino-4-thiazoleglyoxylic acid (Z)-O-[2-[(3,4-dihydroxyphenyl)sulphonamido]ethyl] oxime used as the starting material was prepared as follows:

a) A solution of 10 g of 2-amino-4-thiazoleglyoxylic acid ethyl ester (Z)-O-(2-bromoethyl) oxime in 100 ml of methylene chloride was treated in succession with 3.14 ml of triethylamine and a solution of 8.8 g of trityl chloride in 50 ml of methylene chloride. The reaction solution was stirred at 20° C. for 18 hours, washed with water, and then dried over magnesium sulphate. The solvent was removed in a vacuum, upon which crude 2-(tritylamino)-4-thiazoleglyoxylic acid ethyl ester (Z)-O-(2-bromoethyl) oxime was obtained as an oil.

b) A solution of 17.5 g of 2-(tritylamino)-4-thiazoleglyoxylic acid ethyl ester (Z)-O-(2-bromoethyl) oxime and 5 g of sodium azide in 200 ml of N,N-dimethylformamide was stirred at 50° C. for 15 hours. The reaction solution was cooled to 20° C. and partitioned between ethyl acetate and water. The organic phase was dried over sodium sulphate and the solvent was removed in a vacuum. Crude 2-(tritylamino)-4-thiazoleglyoxylic acid ethyl ester (Z)-O-(2-azido-ethyl) oxime was obtained as an oil.

c) 16.4 g of 2-(tritylamino)-4-thiazoleglyoxylic acid ethyl ester (Z)-O-(2-azidoethyl) oxime were hydrogenated for 3.5 hours under normal pressure in 300 ml of methanol in the presence of 2.5 g of palladium/carbon (5%). The catalyst was filtered off and the solvent was removed in a vacuum. The residue was crystallized from carbon tetrachloride/petroleum ether (low-boiling). There was obtained 2-(tritylamino)-4-thiazoleglyoxylic acid ethyl ester (Z)-O-(2-aminoethyl) oxime as white crystals having a melting point of 126°–144° C.

d) 1.17 g of 3,4-diacetoxy-benzenesulphonyl chloride were added to a solution of 6.0 g of 2-(tritylamino)-4-thiazoleglyoxylic acid ethyl ester (Z)-O-(2-aminoethyl) oxime and 0.49 g of 4-dimethylamino-pyridine in 50 ml of N,N-dimethylformamide. The reaction solution was stirred at 20° C. for 3 hours, 10 ml of 2N sodium hydroxide solution were then added, and the solution was stirred at 20° C. for an additional hour. Then, 20 ml of water were added and the pH of the reaction mixture was lowered to 3 by the addition of 3N hydrochloric acid. The resulting precipitate was filtered off under suction, washed with a small amount of water and then heated to 50° C. for 40 minutes in 60 ml of 80% aqueous acetic acid. The mixture was cooled to 20° C. and evaporated completely in a vacuum. The residue was dissolved in 30 ml of methanol and treated in an ice bath with a total of 180 ml of diethyl ether. The precipitate was filtered off under suction, suspended in a small amount of water and brought into solution by the dropwise addition of 2N sodium hydroxide solution. The solution of pH 7.5 was applied to a MCI gel column (CHP2OP) conditioned with 1% aqueous acetic acid and chromatographed according to the procedure described in the first paragraph of this Example. The product was eluted with a 9:1 (v/v) water/acetonitrile mixture. The pure fractions were concentrated completely in a vacuum and the solid residue was crystallized from methanol/diethyl ether. There was obtained 2-amino-4-thiazoleglyoxylic acid (Z)-O-[2-[(3,4-dihydroxyphenyl)sulphonamido]ethyl] oxime as white crystals of melting point 92°–94° C. (decomposition).

$^1$H NMR (DMSO-d$_6$) δ2.94 (dd, J=7 and 5 Hz); 4.01 (t. J=7 Hz, 1H); 6.83 (s, 1H); 6.87 (d, J=9 Hz, 1H); 7.09 (dd, J=9 and 1.5 Hz, 1H); 7.18 (d, J=1.5 Hz, 1H); 7.25 (broad s, 2H); 7.44 (t, J=5 Hz, 1H); 9.89 (broad s, 1H) ppm.

EXAMPLE 17

A mixture of 146 mg of (6R,7R)-7-[(Z)-2-(2-amino-4-thiazolyl)-2-[(2-iodoethoxy)imino]acetamido]-3-[[[2-(hydroxymethyl)-5-methyl-s-triazolo[1,5-a]pyrimidin-7-yl]thio]methyl]-8-oxo-5-thia-1-azabicyclo[4.2.0]oct-2-ene-2-carboxylic acid, 75 mg of 2.2-diphenyl-1.3-benzodioxol-5-sulphinic acid lithium salt and 24 mg of sodium hydrogen carbonate in 0.5 ml of N,N-dimethylformamide was stirred at 20° C. for 24 hours. The reaction mixture was treated with 5 ml of water and the pH of the mixture was lowered to 3 by the addition of 3N hydrochloric acid. The resulting precipitate was filtered off under suction, washed with a small amount of water and then dissolved in 4 ml of water with the addition of small amount of 2N sodium hydroxide solution. This solution, of pH 7.5, was applied to a MCI gel column (CHP2OP) conditioned with 1% aqueous acetic acid and chromatographed according to the procedure described in Example 16. The fraction eluted with a 1:1 (v/v) water/acetonitrile mixture was concentrated in a vacuum and lyophilized. The lyophilizate was dissolved in 90% aqueous trifluoroacetic acid and the solution was stirred at 20° C. for 20 minutes. The solvents were removed in a vacuum and the residue was partitioned between ethyl acetate and 2% sodium hydrogen carbonate solution. The aqueous phase was chromatographed according to the procedure described in Example 16. After concentration and lyophilization of the pure fractions, there was obtained (6R,7R)-7-[(Z)-2-(2-amino-4-thiazolyl)-2-[[2-[(3.4-dihydroxyphenyl)sulphonyl]ethoxy]imino]acetamido]-3-[[[2-(hydroxymethyl)-5-methyl-s-triazolo[1,5-a]pyrimidin-7-yl]thio]methyl]-8-oxo-5-thia-1-azabicyclo[4.2.0]oct-2-ene-2-carboxylic acid as a white powder.

$^1$H NMR (DMSO-d$_6$) δ2.58 (s, 3H); 3.53 (m, 3H); 3.78 (d, J=18 Hz, 1H); 4.21 (m, 2H); 4.33 (d, J=13 Hz, 1H); 4.50 (d, J=13 Hz, 1H); 4.62 (s, 2H); 5.17 (d, J=5 Hz, 1H); 5.55 (broad s, 1H); 5.78 (dd, J=8 and 5 Hz, 1H); 6.78 (s, 1H); 6.94 (d, J=8 Hz, 1H); 7.18–7.28 (m, 6H); 9.50 (d, J=8 Hz, 1H); 9.85 (broad s, 1H); 10.20 (broad s, 1H) ppm.

The (6R,7R)-7-[(Z)-2-(2-amino-4-thiazolyl)-2-[(2-iodoethoxy)imino]acetamido]-3-[[[2-(hydroxymethyl)-S-methyl-s-triazolo[1.5-a]pyrimidin-7-yl]thio]methyl]-8-oxo-5-thia-1-azabicyclo[4.2.0]oct-2-ene-2-carboxylic acid used as the starting material was prepared as follows:

a) A solution of 3.41 g of 2-amino-4-thiazoleglyoxylic acid (Z)-O-(2-iodoethyl) oxime in 50 ml of N,N-dimethylformamide was cooled to 0° C. and treated in succession with 1.36 g of 1-hydroxy-benzotriazole and 2.04 g of N,N'-dicyclohexylcarbodiimide. The reaction mixture was stirred at 0° C. for 2 hours, upon which a precipitate formed, and it was then treated with a solution, pre-cooled to 0° C., of 4.08 g of (6R,7R)-7-amino-3-[[[(2-hydroxymethyl)-5-methyl-s-tria-zolo[1,5-a]pyrimidin-7-yl]thio]methyl]-8-oxo-5-thia-1-azabicyclo[4.2.0]oct-2-ene-2-carboxylic acid and 1.1 g of triethylamine in 40 ml of N,N-dimethylformamide. The mixture was stirred at 0° C. for 3 hours. The resulting precipitate was filtered off under suction and the filtrate was poured into 400 ml of water. The pH of the solution was lowered to 3.0 by the addition of 3N hydrochloric acid. After stirring in an ice bath for 10 minutes, the precipitate was filtered off under suction and washed with water. The residue on the filter was suspended in a small amount of water and dissolved by the slow addition of about 2 ml of 2N sodium hydroxide solution. This solution, of pH 7.5, was applied to a MCI gel column (CHP2OP) conditioned with 1% aqueous acetic acid and chromatographed according to the procedure described in Example 16. The product was eluted with a 4:1 (v/v) water/acetonitrile mixture. The product fractions were concentrated in a vacuum and the product was precipitated by acidifying the solution to pH 2.8 with 3N hydrochloric acid. (6R,7R)-7-[(Z)-2-(2-Amino-4-thiazolyl)-2-[(2-iodoethoxy)imino]acetamido]-3-[[[2-(hydroxymethyl)-5-methyl-s-triazolo[1,5-a]pyrimidin-7-yl]thio]methyl]-8-oxo-5-thia-1-azabicyclo[4.2.0]oct-2-ene-2-carboxylic acid was isolated as a beige powder.

$^1$H NMR (DMSO-d$_6$): δ2.58 (s, 3H); 3.35 (t, J=7 Hz, 2H); 3.58 (d, J=14 Hz, 1H); 3.76 (d, J=14 Hz, 1H); 4.27 (t, J=7 Hz, 2H); 4.35 (d, J=11 Hz, 1H); 4.44 (d, J=11 Hz, 1H); 4.62 (s, 2H); 5.19 (d, J=4 Hz, 1H); 5.54 (broad s, 1H); 5.81 (dd, J=8 and 4 Hz, 1H); 6.79 (s, 1H); 7.27 (broad s, 3H); 9.64 (d, J=8 Hz, 1H) ppm.

The 2.2-diphenyl-1.3-benzodioxol-5-sulphinic acid lithium salt used as the starting material was prepared as follows:

a) 18.75 g of N-bromosuccinimide are added to a solution of 27.4 g of 2,2-diphenyl-1,3-benzodioxol in 80 ml of chloroform and the mixture was boiled at reflux for 20 hours. The reaction mixture was cooled and the separated succinimide was filtered off. The filtrate was washed with water, dried over sodium sulphate and the solvent was removed in a vacuum. By crystallization of the residue from ethanol, there was obtained 5-bromo-2,2-diphenyl-1,3-benzodioxol as white crystals of melting point 88–89° C.

b) A solution of 14.13 g of 5-bromo-2,2-diphenyl-1,3-benzodioxol in 60 ml of diethyl ether was added dropwise at −50° C. within 5 minutes to a mixture of 24 ml of 1.7M butyllithium/hexane solution and 40 ml of diethyl ether. The reaction solution was stirred for 40 minutes, during which period the temperature was allowed to rise to −15° C. The solution was again cooled to −50° C. and then sulphur dioxide was conducted through the solution for 15 minutes, upon which a white precipitate formed. The reaction mixture was warmed to 20° C. and excess sulphur dioxide was driven off by means of a weak stream of argon. The mixture was suction filtered and the material on the suction filter was washed with diethyl ether and dried in a vacuum. There was obtained 2,2-diphenyl-1,3-benzodioxol-5-sulphic acid lithium salt as a white, amorphous material of melting point 120°–130° C. (decomposition).

$^1$H NMR (DMSO-d$_6$) δ6.92 (d,J=8Hz, 1H); 6.97(dd, J=8 und 1 Hz, 1H); 7.08 (d,J=1 Hz, 1H); 7.35–7.6 (m, 15H) ppm

EXAMPLE A

Manufacture of dry ampoules for intramuscular administration:

A lyophilizate of 1 g of the sodium salt of (6R,7R)-7-[(Z)-2-(2-amino-4-thiazolyl)-2-[[[(3,-4-dihydroxyphenyl)sulphonyl]methoxy]imino]acetamido]-3-[[(2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid is prepared in the usual manner and filled into an ampoule. Prior to the administration, the lyophilizate is treated with 2.5 ml of a 2% aqueous lidocaine hydrochloride solution.

The same procedure is also used for (6R,7R)-7-[(Z)-2-(2-amino-4-thiazolyl)-2-[[[(3,4-dihydroxyphenyl)sulphonyl]methoxy]imino]acetamido]-3-[[[2-(hydroxymethyl)-5-methyl-5-thiazolo[1,5-a]pyrimidin-7-yl]thio]methyl]-8-oxo-5-thia-1-azabicyclo[4.2.0]oct-2-ene-2-carboxylic acid monosodium salt.

I claim:

1. A compound of the formula

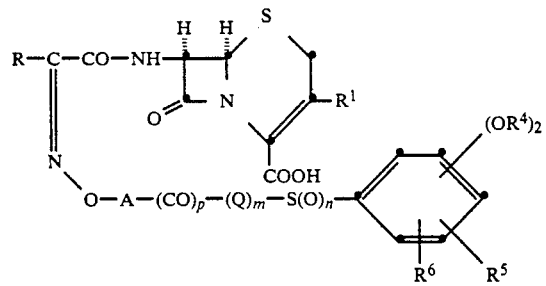

wherein R is a phenyl group or a phenyl group which is mono-, di-, or trisubstituted with halogen, hydroxy, nitro, amino, cyano, trifluoromethyl, lower alkyl or lower alkoxy, a 5-membered aromatic heterocyclic group which has as the hetero (non-carbon) ring member(s) an oxygen or sulphur atom or an imino or lower alkylimino group and optionally one or two nitrogen atoms, or a 6-membered aromatic heterocyclic group, which has one to three nitrogen atoms as the hetero ring member(s); $R^1$ is —CH$_2$—S—R″ wherein R″ is a monocyclic or bicyclic heterocyclic aromatic group which is unsubstituted or substituted with lower alkyl, lower alkoxy, lower alkanediyl, halogen, trifluoromethyl, hydroxy, oxo, carboxy, lower alkoxycarbonyl, carbamoyl, N-(lower alkyl)carbamoyl), N,N-di(lower alkyl)carbamoyl, amino, lower alkylamino, di(lower alkyl)amino, mercapto, lower alkythio, lower hydroxyalkyl, lower aminoalkyl, lower alkylamino-lower alkyl, di(-lower alkyl) amino-lower alkyl, lower carboxyalkyl, carbamoyl-lower alkyl, N-(lower alkyl)carbamoyl-lower alkyl, and N,N-di(lower alkyl)carbamoyl-lower alkyl or sulpho-lower alkyl, A is lower alkylene or C$_{3-7}$-cycloalkylene which is optionally substituted with carboxy, carbamoyl, lower alkylcarbamoyl or di(lower alkyl)carbamoyl; Q is lower alkylene or C$_{3-7}$-cycloalkylene which is optionally substituted with carboxy, carbamoyl, lower alkylcarbamoyl or di(lower alkyl)carbamoyl; or the —NR$^2$—, or —NR$^2$NR$^3$—; R$^2$ and R$^3$ are independently hydrogen or lower alkyl; p and m are zero or 1; n is zero, 1 or 2; R$^4$ is hydrogen, lower alkanoyl or tri(lower alkyl)silyl; two R$^4$ groups together represent diphenylmethylene; R$^5$ is hydrogen, lower alkyl, hydroxy, lower alkoxy, halogen, nitro, —O-COR$^7$, —OCOOR$^{71}$, —N(R$^7$)$_2$, —NHCOR$^7$, —NHCOOR$^{71}$, —COR$^7$, —SR$^7$, —SOR$^7$, SO$_2$R$^7$, —SO$_3$H, —COOR$^7$ or —CON(R$^7$)$_2$, R$^6$ is hydrogen, lower alkyl or halogen, R$^7$ is hydrogen or lower alkyl and R$^{71}$ is lower alkyl, and the two —OR$^4$ groups are attached to the phenyl ring via adjacent carbon atoms, or a 1-(lower alkanoyloxy)-lower alkyl ester, a 1-(lower alkoxycarbonyloxy)lower alkyl ester, a lactonyl ester, a 1-(lower alkoxy)-lower alkyl ester, a 1-(lower alkanoylamino)-lower alkyl ester, a benzyl ester, a cyanomethyl ester or a (2-oxo-1,3-dioxol-4-yl)-methyl ester or pharmaceutically acceptable salt, or a hydrate of any of the foregoing.

2. A compound according to claim 1, wherein R$^4$ is lower alkanoyl or tri(lower alkyl)silyl.

3. A compound according to claim 1, wherein A is lower alkylidene, n is 2, either m or p is zero or m and p are 1, Q is the group —NR$^2$NR$^3$—, and R$^2$ and R$^3$ are independently hydrogen.

4. A compound according to claim 3, wherein R$^4$, R$^5$ and R$^6$ each are hydrogen.

5. A compound according to claim 4, wherein the two —OR$^4$ groups are situated in positions 3 and 4 of the phenyl ring.

6. A compound according to claim 5, wherein A is methylene or isopropylidene.

7. A compound according to claim 1, wherein the substituent in the 7-position is one of the following:

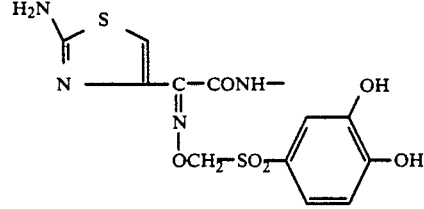

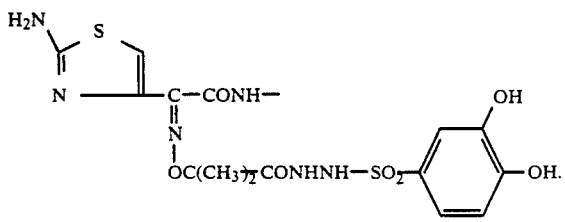

8. A compound according to claim 1, wherein the substituent in the 7-position is the following:

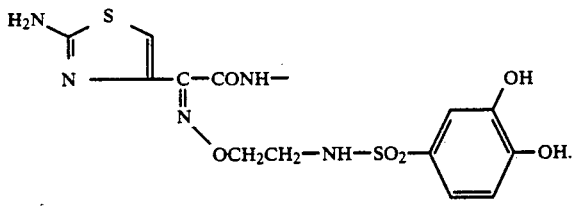

9. A compound according to claim 1, wherein R" is a bicyclic, 8- to 10-membered, partially unsaturated or aromatic heterocyclic group which contains an oxygen or sulphur atom and/or 1 to 5 nitrogen atoms as the non-carbon ring member(s).

10. A compound according to claim 9, wherein the heterocyclic group R" is unsubstituted or mono-, di- or trisubstituted with lower alkyl, lower alkoxy, lower alkanediyl, halogen, trifluoromethyl, hydroxy, oxo, carboxy, lower alkoxycarbonyl, carbamoyl, N-(lower alkyl)carbamoyl, N,N-di(lower alkyl)carbamoyl, amino, lower alkylamino, di(lower alkyl)amino, mercapto, lower alkylthio, lower hydroxyalkyl, lower aminoalkyl, lower alkylamino-lower alkyl, di(lower alkyl)amino-lower alkyl, lower carboxyalkyl, carbamoyl-lower alkyl, N-(lower alkyl)carbamoyl-lower alkyl, N,N-di(lower alkyl)-carbamoyl-lower alkyl or sulpho-lower alkyl.

11. A compound according to claim 10, wherein the heterocyclic group R" has one of the following formulae:

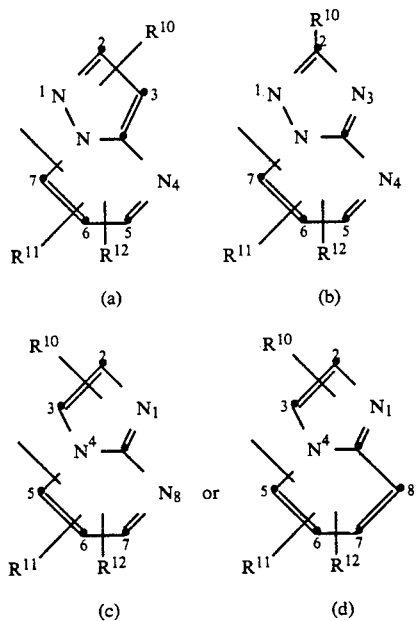

wherein $R^{10}$ is hydrogen, amino, carboxy, lower alkoxycarbonyl, carbamoyl, hydroxymethyl, N-(lower alkyl)carbamoyl, or N,N-di(lower alkyl)-carbamoyl and $R^{11}$ and $R^{12}$ are hydrogen, lower alkyl or trifluoromethyl or together represent a $C_{3-4}$-alkanediyl group.

12. A compound according to claim 11, wherein $R^{10}$ is hydrogen, amino, carboxy, lower alkoxycarbonyl, carbamoyl, N-(lower alkyl)carbamoyl or N,N-di(lower alkyl)carbamoyl.

13. A compound according to claim 11, wherein the heterocyclic groups of formulae (a) and (b) are attached to the sulphur atom via the 5- or 7-ring position, those of formula (c) are attached via 5- or 7-ring position, and those of formula (d) are attached via the 5- or 8-ring position.

14. A compound according to claim 11, wherein R" is 2-carbamoyl-5-methyl-s-triazolo[1,5-a]-pyrimidin-7-yl.

15. A compound according to claim 11, wherein R" is 2-(hydroxymethyl)-5-methyl-s-triazolo-[1,5-a]pyrimidin-7-yl.

16. A compound according to claim 11, wherein $R^{10}$ is situated in the 3-ring position when the heterocyclic group is one of the formula (a), (c) or (d).

17. A compound according to claim 11, wherein $R^{10}$ is carbamoyl.

18. A compound according to claim 13, wherein $R^{10}$ is hydroxymethyl.

19. A compound according to any one of claim 11, wherein $R^{11}$ is hydrogen and $R^{12}$ is lower alkyl or trifluoromethyl.

20. A compound according to claim 1, wherein R is 2-amino-4-thiazolyl.

21. A compound according to claim 1, which is (6R,7R)-7-[(Z)-2-(2-amino-4-thiazolyl)-2-[[[(3,4-dihydroxyphenyl)sulphonyl]methoxy]imino]acetamido]-3-[[(2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid, or a pharmaceutically acceptable salt or hydrate thereof.

22. A compound according to claim 1, which is (6R,7R)-7-[(Z)-2-(2-amino-4-thiazolyl)-2-[[[(3,4-dihydroxyphenyl)sulphonyl]methoxy]imino]acetamido]-3-[[(2,5-dihydro-6-hydroxy-2-methyl-5-oxo-as-triazin-3-yl)thio]methyl]-8-oxo-5-thia-1-azabicyclo[4.2.0]oct-2-ene-2-carboxylic acid, or a pharmaceutically acceptable salt or hydrate thereof.

23. A compound according to claim 1, which is (6R,7R)-7-[(Z)-2-(2-amino-4-thiazolyl)-2-[[[(3,4-dihydroxyphenyl)sulphonyl]methoxy]imino]acetamido]]-3-[[(2-carboxy-5-methyl-s-triazolo[1,5-a]pyrimidin-7-yl)thio]-methyl]-8-oxo-5-thia-1-azabicyclo[4.2.0]oct-2-ene-2-carboxylic acid, or a pharmaceutically acceptable salt or hydrate thereof.

24. A compound according to claim 1, which is (6R,7R)-7-[(Z)-2-(2-amino-4-thiazolyl)-2-[[[(3,4-dihydroxyphenyl)sulphonyl]methoxy]imino]acetamido]-3-[[(5-methyl-1,3,4-thiadiazol-2-yl)thio]methyl]-8-oxo-5-thia-1-azabicyclo[4.2.0]oct-2-ene-2-carboxylic acid, or a pharmaceutically acceptable salt or hydrate thereof.

25. A compound according to claim 1, which is (6R,7R)-7-[(Z)-2-(2-amino-4-thiazolyl)-2-[[[(3,4-dihydroxyphenyl)sulphonyl]methoxy]imino]acetamido]-3-[[(3-carbamoyl-5-methylpyrazolo[1,5-a]pyrimidin-7-yl)thio]methyl]-8-oxo-5-thia-1-azabicyclo[4.2.0]oct-2-ene-2-carboxylic acid, or a pharmaceutically acceptable salt or hydrate thereof.

26. A compound according to claim 1, which is (6R,7R)-7-[(Z)-2-(2-amino-4-thiazolyl)-2-[[[(3,4-dihydroxyphenyl)sulphonyl]methoxy]imino]acetamido]-3-[[(3-carbamoyl-7-(trifluoromethyl)pyrazolo[1,5-a]pyrimidin-5-yl)thio]methyl]-8-oxo-5-thia-1-azabicyclo[4.2.-0]oct-2-ene-2-carboxylic acid, or a pharmaceutically acceptable salt or hydrate thereof.

27. A compound according to claim 1, which is (6R,7R)-7-[(Z)-2-(2-amino-4-thiazolyl)-2-[[1-[3-[(3,4-dihydroxyphenyl)sulphonyl]carbazolyl]-1-methylethoxy]imino]acetamido]-3-[[(2-carbamoyl)-5-methyl-s-triazolo[1,5-a]pyrimidin-7-yl)thio]methyl]-8-oxo-5-thia- I-azabicyclo[4.2.0]oct-2-ene-2-carboxylic acid, or a pharmaceutically acceptable salt or hydrate thereof.

28. A compound according to claim 1, which is (6R,7R)-7-[(Z)-2-(2-amino-4-thiazolyl)-2-[[[(3,4-dihydroxyphenyl)sulphonyl]methoxy]imino]acetamido]-3-[[(2-(methoxycarbonyl)-5-methyl-s-triazolo[1,5-a]pyrimidin-7-yl]thio)methyl]-8-oxo-5-thia-1-azabicyclo[4.2.0]oct-2-ene-2-carboxylic acid, or a pharmaceutically acceptable salt or hydrate thereof.

29. A compound according to claim 1, which is (6R,7R)-7-[(Z)-2-(2-amino-4-thiazolyl)--2-[[[(3,4-dihydroxyphenyl)sulphonyl]methoxy]imino]acetamido]-3-[[(7-methylpyrazolo[1,5-a]pyrimidin-5-yl)thio]methyl-8-oxo-5-thia-1-azabicyclo[4.2.0]oct-2-ene-2-carboxylic acid, or a pharmaceutically acceptable salt or hydrate thereof.

30. A compound according to claim 1, which is (6R,7R)-7-[(Z)-2-(2-amino-4-thiazolyl)-2-[[[(3,4-dihydroxyphenyl)sulphonyl]methoxy]imino]acetamido]-3-[[(5-methylpyrazolo[1,5-a]pyrimidin-7-yl)thio]methyl]-8-oxo-5-thia-1-azabicyclo[4.2.0]oct-2-ene-2-carboxylic acid, or a pharmaceutically acceptable salt or hydrate thereof.

31. A compound according to claim 1, which is (6R,7R)-7-[(Z)-2-(2-amino-4-thiazolyl)-2-[[[(3,4-dihydroxyphenyl)sulphonyl]methoxy]imino]acetamido]-3-[[(3-carboxy-7-methylpyrazolo[1,5-a]pyrimidin-5-yl)thio]methyl]-8-oxo-5-thia-1-azabicyclo[4.2.0]oct-2-ene-2-carboxylic acid, or a pharmaceutically acceptable salt or hydrate thereof.

32. A compound according to claim 1 which is (6R,7R)-7-[(Z)-2-(2-amino-4-thiazolyl)-2-[[[(-3,4-dihydroxyphenyl)sulphonyl]methoxy]imino]acetamido]-3-[[(2,5-dimethylpyrazolo[1,5-a]pyrimidin-7-yl)thio]methyl]-8-oxo-5-thia-1-azabicyclo[4.2.0]oct-2-ene-2-carboxylic acid or a pharmaceutically acceptable salt or hydrate thereof.

33. A compound according to claim 1, which is (6R,7R)-7-[(Z)-2-(2-amino-4-thiazaolyl)-2-[[[(3,4-dihydroxyphenyl)sulphonyl]methoxy]imino]acetamido]-3-[[(2,8-bis(trifluoromethyl)-4-quinolinyl]thio]methyl-8-oxo-5-thia-1-azabicyclo[4.2.0]oct-2-ene-2-carboxylic acid or a pharmaceutically acceptable salt or hydrate thereof.

34. A compound according to claim 1, which is 3-[[[(6R,7R)-7-[(Z)-2-(2-amino-4-thiazolyl)-2-[[[(3,4-dihydroxyphenyl)sulphonyl]methoxy]imino]acetamido]-2-carboxy-8-oxo-5-thia-1-azabicyclo[4.2.0]oct-2-ene-3-yl]methyl]thio]-1-(carbamoylmethyl)pyridinium betaine, or a pharmaceutically acceptable salt or hydrate thereof.

35. A compound according to claim 1, which is (6R,7R)-7-[(Z)-2-(2-amino-4-thiazolyl)-2-[[[(3,4-di hydroxyphenyl)sulphonyl]methoxy]imino]acetamido]-3-[[[2-(hydroxymethyl)-5-methyl-s-triazolo[1,5-a]pyrimidin-7-yl]thio]methyl]-8-oxo-5-thia-1-azabicyclo[4.2.0]oct-2-ene-2-carboxylic acid, or a pharmaceutically acceptable salt or hydrate thereof.

36. A compound according to claim 1, which is (6R,7R)-7-[(Z)-2-(2-amino-4-thiazolyl)-2-[[2-[(3,4-di hydroxyphenyl)sulphonamido]ethoxy]imino]-acetamido]-3-[[(2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid, or a pharmaceutically acceptable salt of hydrate thereof.

37. A compound according to claim 1, which is (6R,7R)-7-[(Z)-2-(2-amino-4-thiazolyl)-2-[[2-[(3,4-dihydroxyphenyl)-sulphonyl]ethoxy]imino]acetamido]-3-[[[2-(hydroxymethyl)-5methyl-s-triazolo[1,5-a]pyrimidin-7-yl]thio]methyl]-8-oxo-5-thia-1-azabicyclo[4.2.0]oct-2-ene-2-carboxylic acid, or a pharmaceutically acceptable salt or hydrate thereof.

38. A pharmaceutical composition comprising an antibacterially effective amount of a compound of the formula

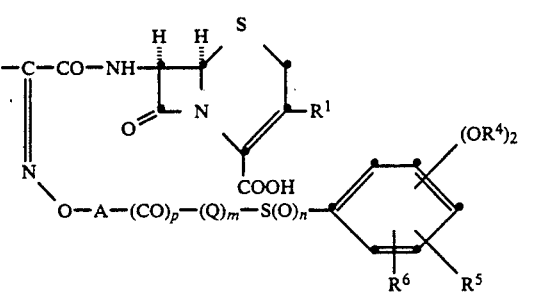

wherein R is a phenyl group or a phenyl group which is mono-, di-, or trisubstituted with halogen, hydroxy, nitro, amino, cyano, trifluoromethyl, lower alkyl or lower alkoxy, a 5-membered aromatic heterocyclic group which has as the hetero (non-carbon) ring member(s) an oxygen or sulphur atom or an imino or lower alkylimino group and optionally one or two nitrogen atoms, or a 6-membered aromatic heterocyclic group, which has one to three nitrogen atoms as the hetero ring member(s); $R^1$ is $—CH_2—S—R''$ wherein $R''$ is a monocyclic or bicyclic heterocyclic aromatic group which is unsubstituted or substituted with lower alkyl, lower alkoxy, lower alkanediyl, halogen trifluoromethyl, hydroxy, oxo, carboxy, lower alkoxycarbonyl, carbamoyl, N-(lower alkyl)carbamoyl), N,N-di(lower alkyl) carbamoyl, amino, lower alkylamino, di(lower alkyl)amino, mercapto, lower alkylthio, lower hydroxyalkyl, lower aminoalkyl, lower alkylamino-lower alkyl, di(lower alkyl)amino-lower alkyl, lower carboxyalkyl, carbamoyl-lower alkyl, N-(lower alkyl)carbamoyl-lower alkyl, N,N-di(lower alkyl)carbamoyl-lower alkyl, or sulpho-lower alkyl; A is lower alkylene or $C_{3-7}$-cycloalkylene which is optionally substituted with carboxy, carbamoyl, lower alkylcarbamoyl or di(lower alkyl)carbamoyl; Q is lower alkylene or $C_{3-7}$ cycloalkylene which is optionally substituted with carboxy, carbamoyl, lower alkylcarbamoyl or di(lower alkyl)carbamoyl, or the $—NR^2—$, $—NR^2N-R^3—$; $R^2$ and $R^3$ are independently hydrogen or lower alkyl; p and m are zero or 1; n is zero, 1 or 2; $R^4$ is hydrogen, lower alkanoyl or tri(lower alkyl)silyl; two $R^4$ groups together represent diphenylmethylene; $R^5$ is hydrogen, lower alkyl, hydroxy, lower alkoxy, halogen, nitro, $—OCOR^7$, $—OCOOR^{71}$, $—N(R^7)_2$, $—NHCOR^7$, $—NHCOOR^{71}$, $—COR^7$, $—SR^7$, $—SOR^7$, $—SO_2R^7$, $—SO_3H$, $—COOR^7$ or $—CON(R^7)_2$, $R^6$ is hydrogen, lower alkyl or halogen, $R^7$ is hydrogen or lower alkyl and $R^{71}$ is lower alkyl, and the two $—OR^4$ groups are attached to the phenyl ring via adjacent carbon atoms, or a 1-(lower alkanoyloxy)-lower alkyl ester, a 1-(lower alkoxycarbonyloxy)lower alkyl ester, a lactonyl ester, a 1-(lower alkoxy)-lower alkyl ester, a 1-(lower alkanoylamino)-lower alkyl ester, a benzyl ester, a cyanomethyl ester or a (2-oxo-1,3-dioxol-4-yl)-methyl ester or pharmaceutically acceptable salt, or a hydrate of any of the foregoing, together with an inert carrier.

39. A method of treating a bacterial infection in a host comprising administering to the host an effective amount of a compound of the formula

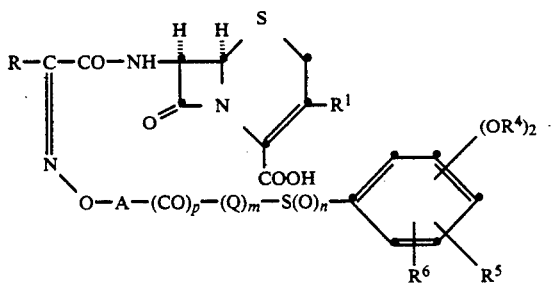

wherein R is a phenyl group or a phenyl group which is mono-, di-, or trisubstituted with halogen, hydroxy, nitro, amino, cyano, trifluoromethyl, lower alkyl or lower alkoxy, a 5-membered aromatic heterocyclic group which has as the hetero (noncarbon) ring member(s) an oxygen or sulphur atom or an imino or lower alkylimino group and optionally one or two nitrogen atoms, or a 6-membered aromatic heterocyclic group, which has one to three nitrogen atoms as the hetero ring member(s); $R^1$ is $-CH_2-S-R''$ wherein $R''$ is a monocyclic or bicyclic heterocyclic aromatic group which is unsubstituted or substituted with lower alkyl, lower alkoxy, lower alkanediyl, halogen, trifluoromethyl, hydroxy, oxo, carboxy, lower alkoxycarbonyl, carbamoyl, N-(lower alkyl)carbamoyl, N,N-di(lower alkyl) carbamoyl, amino, lower alkylamino, di(lower alkyl)amino, mercapto, lower alkylthio, lower hydroxyalkyl, lower aminoalkyl, lower alkylamino-lower alkyl, di(lower alkyl) amino-lower alkyl, lower carboxyalkyl, carbamoyl-lower alkyl, N-(lower alkyl)carbamoyl-lower alkyl, N,N-di(lower alkyl)carbamoyl-lower alkyl or sulpho-lower alkyl; A is lower alkylene or $C_{3-7}$-cycloalkylene which is optionally substituted with carboxy, carbamoyl, lower alkylcarbamoyl or di(lower alkyl)carbamoyl; Q is lower alkylene or $C_{3-7}$-cycloalkylene which is optionally substituted with carboxy, carbamoyl, lower alkylcarbamoyl or di(lower alkyl)carbamoyl, or the $-NR^2-$, or $-NR^2NR^3-$; $R^2$ and $R^3$ are independently hydrogen or lower alkyl; p and m are zero R 1; n is zero, 1 or 2; $R^4$ is hydrogen, lower alkanoyl or tri(lower alkyl)silyl; two $R^4$ groups together represent diphenylmethylene; $R^5$ is hydrogen, lower alkyl, hydroxy, lower alkoxy, halogen, nitro, $-OCOR^7$, $-OCOOR^{71}$, $-N(R^7)_2$, $-NHCOR^7$, $-NHCOOR^{71}$, $-COR^7$, $-SR^7$, $-SOR^7$, $-SO_2R^7$, $-SO_3H$, $-COOR^7$, or $-CON(R^7)_2$, $R^6$ is hydrogen, lower alkyl or halogen, $R^7$ is hydrogen or lower alkyl and $R^{71}$ is lower alkyl, and the two $-OR^4$ groups are attached to the phenyl ring via adjacent carbon atoms, or a 1-(lower alkanoyloxy)-lower alkyl ester, a 1-(lower alkoxycarbonyloxy)lower alkyl ester, a lactonyl ester, a 1-(lower alkoxy)-lower alkyl ester, a 1-(lower alkanoylamino)-lower alkyl ester, a benzyl ester, a cyanomethyl ester or a (2-oxo-1,3-dioxol-4-yl)-methyl ester or pharmaceutically acceptable salt, or a hydrate or any of the foregoing.

40. A pharmaceutical composition according to claim 38, wherein $R^4$ is hydrogen, lower alkanoyl or tri(lower alkyl)silyl.

41. A pharmaceutical composition according to claim 38, wherein A is lower alkylidene, n is 2, either m or p is zero or m and p are 1, Q is the group $-NR^2NR^3-$, and $R^2$ and $R^3$ are independently hydrogen.

42. A pharmaceutical composition according to claim 38, wherein $R^4$, $R^5$ and $R^6$ are each hydrogen.

43. A pharmaceutical composition according to claim 38, wherein the two $-OR^4$ groups are situated in positions 3 and 4 of the phenyl ring.

44. A pharmaceutical composition according to claim 38, wherein A is methylene or isopropylidene.

45. A method of treating a bacterial infection in a host according to claim 39, wherein $R^4$ is hydrogen, lower alkanoyl or tri(lower alkyl)silyl.

46. A method of treating a bacterial infection in a host according to claim 39, wherein A is lower alkylidene, n is 2, either m or p is zero or m and p are 1, Q is the group $-NR^2NR^3-$, and $R^2$ and $R^3$ are independently hydrogen.

47. A method of treating a bacterial infection in a host according to claim 39, wherein $R^4$, $R^5$ and $R^6$ each are hydrogen.

48. A method of treating a bacterial infection in a host according to claim 39, wherein the two $-OR^4$ groups are situated in positions 3 and 4 of the phenyl ring.

49. A method of treating a bacterial infection in a host according to claim 39, wherein A is methylene or isopropylidene.

* * * * *